US010208303B2

(12) United States Patent
Stelling

(10) Patent No.: US 10,208,303 B2
(45) Date of Patent: Feb. 19, 2019

(54) SOLID-CORE RING-MAGNET

(71) Applicant: Alpaqua Engineering, LLC, Beverly, MA (US)

(72) Inventor: Olaf Stelling, Beverly Farms, MA (US)

(73) Assignee: Alpaqua Engineering, LLC, Beverly, MA (US)

( * ) Notice: Subject to any disclaimer, the term of this patent is extended or adjusted under 35 U.S.C. 154(b) by 0 days.

(21) Appl. No.: 16/116,206

(22) Filed: Aug. 29, 2018

(65) Prior Publication Data

US 2018/0362964 A1    Dec. 20, 2018

Related U.S. Application Data

(63) Continuation of application No. 15/497,858, filed on Apr. 26, 2017, now Pat. No. 10,087,438, which is a
(Continued)

(51) Int. Cl.
*C12N 15/10* (2006.01)
*C12Q 1/6806* (2018.01)
(Continued)

(52) U.S. Cl.
CPC ........ *C12N 15/1013* (2013.01); *B01L 3/5085* (2013.01); *C12Q 1/6806* (2013.01);
(Continued)

(58) Field of Classification Search
CPC .... H01F 7/02; H01F 7/0278; B01L 2400/043; B01L 3/502761; B01L 2200/0668;
(Continued)

(56) References Cited

U.S. PATENT DOCUMENTS 5,519,373 A    5/1996  Miyata
5,705,062 A    1/1998  Knobel
(Continued)

FOREIGN PATENT DOCUMENTS

DE    20 2014 102 945 U1    8/2014
EP          0 589 636 A1    3/1994
(Continued)

OTHER PUBLICATIONS

PCT International Search Report for PCT PCT/US2015/0556112, dated Oct. 14, 2015, Alpaqua Engineering, LLC.
(Continued)

*Primary Examiner* — Sally A Merkling
(74) *Attorney, Agent, or Firm* — Antoinette G. Giugliano; AGG Intellectual Property Law

(57) ABSTRACT

A solid-core ring-magnet having one or more cavities is provided. The magnet can have an overall cylindrical shape or a rectangular-prism shape. In either case, a portion of cavity walls of the magnet are ring shaped, causing the magnetic field lines to emanate from the magnet in the shape of a ring. The diameter of the ring shaped cavities can be constant throughout, constant through a portion of the cavity, variant throughout, or variant through a portion of the cavity. The cavities open to the end of the magnet, and terminate toward the core of the magnet. Also provided are systems and kits having solid-core ring-magnets. Methods of purifying a macromolecule using the solid-core ring-magnets are also provided.

22 Claims, 14 Drawing Sheets

Related U.S. Application Data continuation of application No. 14/515,256, filed on Oct. 15, 2014, now Pat. No. 9,663,780.

(51) Int. Cl.
*H01F 7/02* (2006.01)
*B01L 3/00* (2006.01)

(52) U.S. Cl.
CPC ........ *H01F 7/02* (2013.01); *B01L 2200/0631* (2013.01); *B01L 2300/0809* (2013.01); *B01L 2300/0829* (2013.01); *B01L 2300/0832* (2013.01); *B01L 2300/0858* (2013.01)

(58) Field of Classification Search
CPC ........... B01L 3/5085; B01L 2300/0829; C12N 15/1013; C12N 15/1003; G01N 35/0098; G01N 33/54326; G01N 1/405; G01N 2035/00564; G01N 2035/103; C12Q 1/6806; C12Q 2563/143; B03C 1/288; B03C 2201/18; B03C 1/01; B03C 1/0332; B03C 2201/26; B03C 1/02; B03C 1/002; B03C 1/286; Y10T 436/25375; Y10T 137/8376; B01D 35/06; C07B 63/00; H02K 15/03; H02K 1/2733; Y10S 436/809; Y10S 428/90; B01F 13/0809; B01F 13/0818
See application file for complete search history.

(56) References Cited

U.S. PATENT DOCUMENTS

| | | | |
|---|---|---|---|
| 5,733,442 A | 3/1998 | Shukla | |
| 6,255,478 B1 | 7/2001 | Komai et al. | |
| 6,764,859 B1 | 7/2004 | Kreuwel et al. | |
| 6,870,047 B2 | 3/2005 | Kleiber et al. | |
| 7,384,559 B2 | 6/2008 | a Brassard | |
| 7,474,184 B1 * | 1/2009 | Humphries | B03C 1/002 335/306 |
| 7,551,051 B2 | 6/2009 | Ugai et al. | |
| 7,718,072 B2 | 5/2010 | Safar et al. | |
| 8,062,846 B2 | 11/2011 | Bortolin et al. | |
| 8,071,395 B2 | 12/2011 | Davis et al. | |
| 8,597,878 B2 | 12/2013 | Hillebrand et al. | |
| 8,703,931 B2 | 4/2014 | Euting et al. | |
| 9,140,634 B1 | 9/2015 | Knippschild et al. | |
| 2005/0072674 A1 | 4/2005 | Heins et al. | |
| 2006/0055266 A1 | 3/2006 | Iwami et al. | |
| 2007/0218566 A1 | 9/2007 | Barten et al. | |
| 2008/0171337 A1 | 7/2008 | Miyazaki et al. | |
| 2008/0206751 A1 | 8/2008 | Squirrell et al. | |
| 2010/0227387 A1 | 9/2010 | Safar et al. | |
| 2010/0311608 A1 | 12/2010 | Osada et al. | |
| 2014/0186236 A1 | 7/2014 | Euting et al. | |

FOREIGN PATENT DOCUMENTS

| | | |
|---|---|---|
| EP | 1404450 B1 | 11/2005 |
| EP | 2082806 A2 | 7/2009 |
| EP | 2 565 260 A2 | 3/2013 |
| WO | WO 1996/15440 | 5/1996 |
| WO | WO 2000/23807 | 4/2000 |
| WO | WO 2003/044537 A1 | 5/2003 |
| WO | WO 2005/008209 A2 | 1/2005 |
| WO | WO 2005/008861 A1 | 1/2005 |
| WO | WO 2006/072593 A2 | 7/2006 |
| WO | WO 2014/007074 A1 | 1/2014 |

OTHER PUBLICATIONS

Written Opinion of the International Searching Authority for PCT PCT/US2015/0556112, dated Oct. 14, 2015, Alpaqua Engineering, LLC.

Communication pursuant to Article 94(3) EPC for EP Application No. 15790728.8-, dated May 5, 2018, Alpaqua Engineering, LLC.

* cited by examiner

SOLID-CORE RING-MAGNET

RELATED APPLICATION

This application is a continuation of U.S. application Ser. No. 15/497,858, entitled "SOLID-CORE RING-MAGNET" by Olaf Stelling, filed Apr. 26, 2017, which is a continuation of U.S. application Ser. No. 14/515,256, entitled "SOLID-CORE RING-MAGNET" by Olaf Stelling, filed Oct. 15, 2014. The entire teachings of the above applications are incorporated herein by reference.

BACKGROUND OF THE INVENTION

Isolation of macromolecules (e.g., nucleic acids, such as DNA or RNA, and proteins such as antibodies) is required before they can be used in many applications. For example, sequencing of nucleic acids and restriction digestion of nucleic acids requires or at least benefits from their purification. Nucleic acids can be purified via a variety of methods, including the traditional phenol-chloroform extraction. A relatively modern method of purifying nucleic acids makes use of magnetic beads. In this approach, magnetic beads are coated with a substance to which nucleic acids have affinity under certain conditions, and from which nucleic acids can be separated under different conditions. Employment of magnetic beads in this manner can eliminate a need for centrifugation steps or vacuum filtration steps, can speed up the process, can increase the yields of recovery, and can allow recovery of nucleic acids directly from an initial sample. Centrifugation and vacuum filtration have traditionally been difficult to automate. Magnetic beads can similarly be used for macromolecules other than nucleic acids; they can be used for proteins and complexes of two or more macromolecules.

Use of magnetic beads, for example while preparing samples for DNA sequencing, suffers from requiring collection of DNA from a relatively large volume, from the recovered DNA being diluted in the solution, and from the form of the recovery vessel being restricted based on the purification setup used. A need exists to improve time sensitive, high-throughput applications with the use of magnetic beads. Therefore, there is a need for improved apparatuses and methods that can enable purification of macromolecules in more concentrated solutions and within a wider variety of vessels.

SUMMARY OF THE INVENTION

Macromolecules, such as nucleic acids, especially those of high quality and purity, can be obtained via a variety of methods. In one method, complexes are formed between macromolecules and magnetic beads, and the magnetic beads are separated from a mixture, essentially purifying the macromolecules after their "un-complexation" from the beads through changes in conditions. In an embodiment, the complex between the macromolecules and magnetic beads remains in the vessel in the form of a ring and most of the solution is removed, leaving a high concentration of complex in the vessel.

In an embodiment, the present invention includes a magnet that can be used to isolate/purify macromolecules from a mixture. The mixture, as defined herein, is any aqueous solution that has at least the macromolecule in addition to the solvent. As an example, it can be extracellular matrix. The macromolecules, as defined here, encompass nucleic acids such as DNA or RNA, or proteins such as antibodies. The magnet, in particular, can be used to isolate macromolecules by making them adhere to magnetic beads, after which they can be separated from the mixture. In particular, through changes in the chemical environment macromolecules are made to adhere to the magnetic beads to form a complex. The magnet is then used to attract the complex, and pull them out of solution. In particular, the magnet of the present invention causes the complex to form a ring of bead complexes within the vessel. The solution can then be removed leaving behind the magnetic beads with the macromolecules adhered thereto.

The magnet encompassed by the present invention has a top surface, a bottom surface, a solid core, and one or more cavities. Each cavity starts at a surface and goes toward the center of the magnet, but does not reach the other side thereby leaving a solid core intact. In other words, no tunnel from the top to bottom surfaces is formed and the magnet retains a solid core. The magnet is surrounded by a side wall on its sides not covered by the surfaces (the top and bottom surfaces).

In an embodiment, the magnet has an overall cylindrical shape. In another embodiment, the magnet is shaped like a rectangular prism. In each of these, the cavities are formed. In embodiments, the cavities can have a "U" shape, "V" shape or other irregular shape so long as it can receive the vessel, as described herein. In a particular embodiment, the cavity wall of the inventive magnet has at least a top portion that is ring-shaped, and other portions can be, for example, conical shaped. The cavities are defined by their cavity walls. The cavity wall can include a base surface, which is the innermost part of the cavity wall that terminates the cavity. The cavity walls can have a constant diameter, or they can have varying diameters. In an embodiment, the base surface can be conically shaped; thus, it might have progressively decreasing radii toward the terminus of the cavity. The cavities receive vessels (e.g., Eppendorf tubes, wells of a microplate) which hold a solution. When the vessel is placed in the cavity of the inventive magnet, the volume of the portion of the solution that falls inside or within the cavity and up to the macromolecule/bead ring, in an embodiment, is between about 5 and about 30 micro-liters (e.g., between about 5 and about 25, 20, 15, and 10 micro-liters). In another embodiment, the volume of the cavity itself is between about 5 and about 45 micro-liters (e.g., between about 5 and about 40, 35, 30, 25, 20, 15 micro-liters.

In another embodiment, a system for isolating macromolecules is disclosed. In addition to the magnet, the system can include a vessel for holding a mixture that includes a macromolecule (e.g., DNA). The same types of magnets as encompassed by other embodiments can be included as part of the system as well.

Also disclosed are methods of purifying macromolecules from a liquid sample that contains a mixture. The methods, in an embodiment, include steps of collecting the liquid in a vessel, adding magnetic beads to the sample, and separating the magnetic bead-macromolecule complex from the sample by placing the vessel in a cavity of a magnet. After these steps, the macromolecule can be eluted from the magnetic beads.

In an embodiment, the present invention includes a kit. The kit can comprise a magnet, as described previously, and a vessel for holding liquid samples. In an embodiment, the vessel can be placed into a cavity of a magnet, and a volume of 5 to 35 micro-liters (e.g., between 5 and 35, 5 and 30, 5 and 25, 5 and 20, 5 and 15, 5 and 10 micro-liters) of sample would remain in the portion of the vessel that is within the magnet and up to the band. Magnetic beads can also be added as part of the kit in some embodiments.

Additionally disclosed are magnet plate systems for isolating macromolecules. The systems include at least one magnet as well as a top plate, a support plate, and a base plate. One or more springs wound around one or more shoulder posts can also be included as part of the magnet plate systems. The top plate can include a plurality of magnet receivers, and it can accommodate either cylindrical shaped magnets or block shaped magnets.

There are many advantages provided by the disclosed systems. Better yields of recovered macromolecules, faster recoveries, higher concentrations, and higher purities of recovered macromolecules are attainable as compared to magnets and systems previously available.

BRIEF DESCRIPTION OF THE DRAWINGS

The foregoing and other objects, features, and advantages of the invention will be apparent from the following more particular description of preferred embodiments of the invention, as illustrated in the accompanying drawings in which like parts are referred to by the same reference characters across different views. The drawings are not necessarily to scale, emphasis instead being placed on illustrating the principles of the invention.

DETAILED DESCRIPTION OF THE INVENTION

Figure 1A:
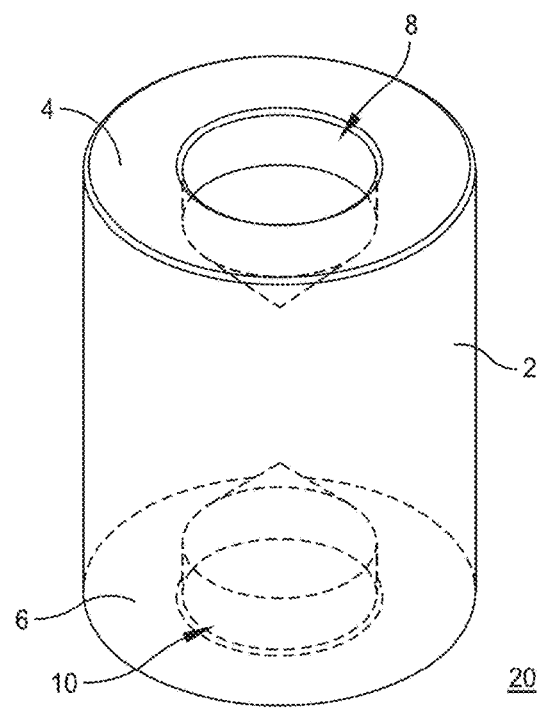
FIG. 1A is a schematic of a perspective view of a solid-core ring-magnet having a cylindrical shape and cylindrical/conical-shaped cavities.

A description of preferred embodiments of the invention follows.

In many molecular biology procedures, macromolecules are needed in a purified form. For example, to prepare a DNA or RNA sample for sequencing, it needs to be extracted from any of a variety of clinical sample types, such as tissue, blood, cheek swabs, sputum, forensic material, FFPE samples etc. The initial extraction from the primary sample is followed by a multitude of enzymatic reactions called library construction. Each enzymatic reaction is followed by another extraction step to isolate conditioned nucleic acid from the reaction mix. The enzymatic reactions are typically followed by amplification (using PCR) and/or size selection (to limit the distribution of fragment sizes to a narrow band of a few hundred basepairs (e.g. 500-700 bp)). The workflow from primary sample to sequencing-ready DNA or RNA may involve from 5-10 separate extraction steps. Throughout the workflow, the overall volume of the mix containing the sample, as well as the sample container can vary significantly; typical volumes range from about 2000 μl to 35 μl. These workflows are often entirely automated to achieve the required precision and throughput. The high degree of automation in sequencing-related workflows has led to widespread adoption of magnetic bead technology for extraction purposes, since alternative protocols require either centrifugation or vacuum filtration, which are not easily automated.

Depending on the nature of the macromolecule to be extracted as well as the matrix they are present in, magnetic beads (more precisely: paramagnetic beads) are coated with moieties (e.g., functional groups, other compounds) to which the macromolecules have affinity. For example, the beads might be coated with a carboxylic acid having moiety such as succinic acid. The coupling between the beads and the macromolecules might also rely on streptavidin-biotin or carbo di-imide chemistry. Exemplary coatings include protein A, protein B, specific antibodies, particular fragments of specific antibodies, streptavidin, nickel, and glutathione. The beads themselves can vary in size, but will have an average diameter (e.g., 1 micro-meter). In some embodiments, the paramagnetic properties of the beads will result from integration of iron into an otherwise non-magnetic substance (e.g., 4% agarose gel). Magnetic beads, as well as those that are already coated with various affinity groups, can be purchased from Sigma-Aldrich Corp. (St. Louis, Mo., USA), Life Technologies (Grand Island, N.Y., USA), Thermo Scientific (Rockford, Ill., USA), EMD-Millipore (Billerica, Mass., USA), and New England Biolabs (Ipswich, Mass., USA).

In one application of the methods of the present invention, molecules (e.g., macromolecules) can be purified using magnetic beads by performing the following steps:

a. mixing the magnetic beads having a particular affinity-conferring coating with the molecule of interest in a container (e.g., a vessel, an Eppendorf tube, a microplate well, a deep well, a PCR well, round-bottom vessel);

b. after the mixing, allowing for specific binding between the beads and the molecules, thus creating bead-molecule complexes;

c. placing the bottom of the vessel inside the cavity of a solid-core ring-magnet;

d. allowing the bead-molecule complexes to aggregate (e.g., segregate) in a ring shape around the perimeter of the bottom of the vessel (or of each vessel if using multiple ones); and e. removing the supernatant, which would have unbound, undesired molecules;

f. performing one or more wash steps by adding a suitable solvent, e.g., ethanol, followed by removal of the same.

Additional steps can include re-suspending the bead-molecule complexes in a solvent, so as to obtain a solution with a desired volume and concentration. One can choose the appropriate solvent so that the binding affinity between the beads and the molecules is decreased, allowing them to dissociate from each other. Or one can repeat the steps above to aggregate the magnetic beads again to allow for additional separations, depending on the buffer chosen.

Also the beads may be used to either bind the component of interest, for example nucleic acid molecules, and during the method one discards the supernatant and elutes the component of interest from the beads. Alternatively, one can let the beads bind to a component that one is trying to discard, leaving only the component of interest in the supernatant. In this case, the supernatant is transferred to a new, clean vessel for use or further experimentation and the magnetic beads with their unwanted molecules are discarded.

The above methods are generally automated using robotic systems (e.g., automated liquid handling workstations) or aspirating/dispensing manifolds. Usable workstations for automation include Agilent Bravo, Apricot Designs TPS-384, Beckman Biomk FX, Tecan Freedom EVO. The steps of the present invention can be done manually e.g., using pipetting to remove/collect the supernatant.

Once a complex is formed between a macromolecule of interest and a magnetic bead (which might be formed via covalent as well as non-covalent bonds), a magnetic field created by a magnet can be employed to concentrate the bead-macromolecule complexes in a portion of the mixture (e.g., in a band in a solution). After that, the supernatant can be aspirated (e.g., via pipetting) and the complexes are separated from the mixture. Subsequently, the macromolecules can be separated from the beads, for example by eluting them via changes in the solution (e.g., buffer composition features such as pH and salt concentration). With currently known methods, this step results in large volumes of eluted macromolecules. The present invention surprisingly allows recovery of an eluate that is of lower volume, of a higher yield, and of a higher concentration. The process of recovery also is sped up with the magnet of the present invention.

The magnet of the present invention, in one embodiment is made from a rare-earth metal such as neodymium. A neodymium magnet can have the chemical composition $Nd_2Fe_{14}B$, where Nd is neodymium, Fe is iron, and B is boron. In some alternative embodiments, the magnet can also be made from samarium (e.g., sintered $SmCo_5$). The magnet can be covered with a protective layer, for example a layer of nickel. Alternative coatings include one or multiple layers, such as nickel, copper, zinc, tin, silver, gold, epoxy resin, or any other suitable material. Such coatings help, among other things, with preventing rusting of the iron component. In each of these embodiments, the full object is referred to as the "magnet". The magnet can have a strength grade which for different embodiments can be N35, N38, N40, N42, N45, N48, N50, or N52. Additional magnets with different grades, such as those with higher N-numbers (those that may be manufactured in the future) or different temperature ranges (H-grades), are also included among the embodiments of the present invention. The magnets (e.g., neodymium magnets) can be sintered or bonded. Magnets can be purchased from K&J Magnetics, Inc., Jamison, Pa. For example, the cavities can be drilled into the magnet with a drill bit.

In one embodiment, shown in FIG. 1A, magnet 20 has two cavities, top cavity 8 and bottom cavity 10. Top cavity 8 descends from the center of top surface 4, while bottom cavity 10 rises from bottom surface 6. The sides of magnet 20 are surrounded by side wall 2. In the embodiment shown in FIG. 1A, both the magnet is cylindrical and a portion of the cavity wall is cylindrical-shaped. The cavities have walls that are in part cylindrical-shaped and in part conical shaped. In an embodiment, the cavity wall can be any shape so long as a portion of the cavity wall has a cylindrical shape to form a magnet field that attracts the beads in a ring shape formation within the vessel. The term "cylindrical-shaped," in this document, is used to refer to three-dimensional structures that have sections that have ring-like (circular) outer boundaries. The term "cylindrical/conical-shaped," refers to a cavity that has both features and in particular, has three-dimensional structures that have sections that have ring-like (circular) outer boundaries and a section of the base that is conical. The axes of the cylindrical sections, as defined, are parallel to the axis of thickness (i.e., between the top surface and the bottom surface planes) of the structure. Additionally, sections that are elliptical to a slight degree (e.g., the two radii differing by less than 5%) are also encompassed in the shape of the cavity. The cavity can be of any shape so long as it can receive a vessel such that, when in use, the magnetic field causes the magnetic beads to form a ring within the vessel.

The overall structure, for magnet 20, is cylindrical when the presence of cavities is ignored. In other words, the volume enclosed inside of the outside wall, bound above by the plane of the top surface (e.g., top plane), and bound below by the plane of the bottom surface (e.g., bottom plane) is cylinder-shaped. When referring to volumes, the terms top surface and bottom surface are used to mean the plane of the top surface and the plane of the bottom surface, respectively.

For clarification, there are two pertinent volumes with respect to the cavities of the magnet of the present invention. The volume of the cavity itself, and the volume of solution in the vessel that, when placed into the magnet, resides generally within the cavity (i.e., between the top plane and the lowest point of the cavity wall), or put another way, from the lowest point of the cavity wall up to the bead ring. In one embodiment, the volume of the cavity itself is between about 5 and about 45 micro-liters (e.g., between about 5 and about 40, 35, 30, 25, 20, 15 micro-liters. In another embodiment, the cavity has a size such that the volume of the solution in the vessel and that which lies within the cavity up to the bead ring, in an embodiment, is between about 5 and about 35 micro-liters (e.g., between about 5 and about 34, 33, 32, 31, 30, 25, 20, 15, 10 micro-liters). The latter also refers to the volume needed in the vessel to cover the macromolecule-bead ring so as to elute the beads from the macromolecules or to perform some other experiment. Note that a space exists between the cavity wall and the vessel placed within the cavity, and so a difference in volume exists between the cavity size and the volume of solution in the vessel and within the top plane. In the embodiment shown in FIG. 1A, two cavities are shown. However, one cavity can be used, in an embodiment, since it creates a place for the vessel to be received. However, two cavities, in another embodiment, are desired so that the magnets can be inserted during assembly in either orientation, i.e., polarity. Accordingly, the present invention involves a magnet with one or more cavities (e.g., two, three, four, five, six, seven, eight, nine, or ten, etc.).

Figure 1B:
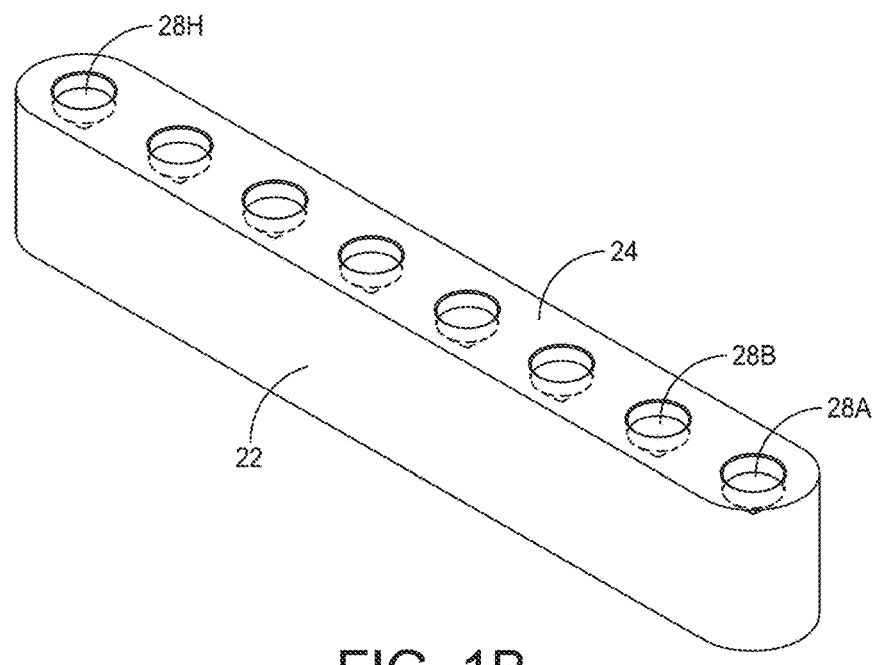
FIG. 1B is a schematic of a perspective view of a solid-core ring-magnet having multiple cylindrical/conical-shaped cavities and an overall rectangular-prism shape.

In other embodiments, while the cavity wall has a portion that is cylindrical shaped, the overall magnet can be block-shaped, a bar, or a prism (e.g., rectangular-prism shaped). One such embodiment is shown in FIG. 1B. Shown are side wall 22, top surface 24, and top cavities (28A, 28B . . . 28H) of magnet 40. Magnet 40 is generally a bar magnet with curved ends and a number of cavities, whereas magnet 20 is a cylindrical magnet with two cavities. With respect to the applications of the magnets, the focus is on the cavity as opposed to the full magnet. Therefore, both the cylindrical magnet (e.g., magnet 20) and the block magnet (e.g., magnet 40) are considered and referred to as solid core magnets because regardless of the shape of the magnet that has cavities, the core is a solid filled magnet. "Solid core magnet" and "solid core ring magnet" are used interchangeably herein. The word "ring" of the phrase "solid core ring magnet" connotes the shape of the top portion of the cavity wall or the ring of the paramagnetic bead/macromolecule complex that it forms. In other words, the term "solid core magnet" in this document refers to magnets that have a solid core and a cavity wall with at least a portion being ring shaped, regardless of whether the magnets are cylindrical shaped or rectangular-prism shaped.

Figure 2A:
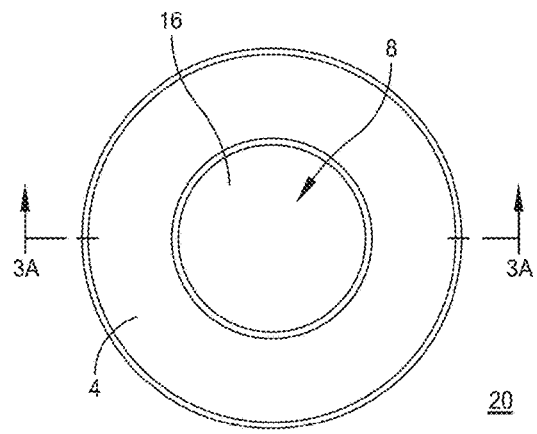
FIG. 2A is a schematic of a top view of a solid-core ring-magnet having a cylindrical shape.

FIG. 2A shows a top view of the magnet shown in FIG. 1A. Visible are top surface 4, top cavity 8, as well as base surface 16 of the top cavity. From this figure, it is apparent that the cavity wall is ring/conical-shaped. A cutout view as generated through the markings "3A" is shown in FIG. 3A.

Figure 2B:
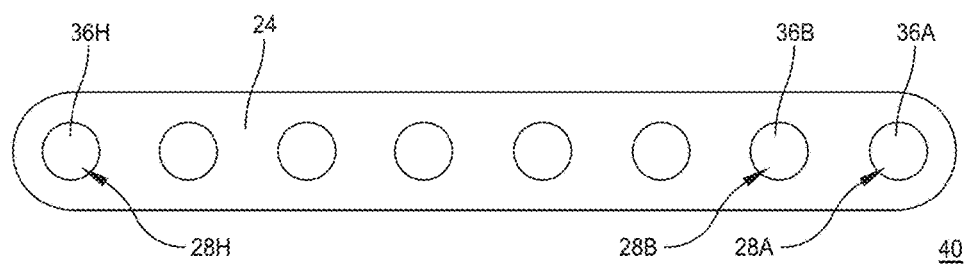
FIG. 2B is a schematic of a top view of a solid-core ring-magnet having multiple cylindrical/conical-shaped cavities and an overall rectangular-prism shape.

FIG. 2B shows a top view of the magnet shown in FIG. 1B. Shown magnet 40 is a block magnet, and has eight cavities. Shown in this figure are top surface 24, top cavities (28A, 28B . . . 28H), and base surfaces (36A, 36B . . . 36H) of the top cavities. Even though the outer boundary of this block magnet is shaped like a rectangular prism, this magnet is also classified herein as a ring-magnet because the cavity walls are ring/conical-shaped.

Figure 3A:
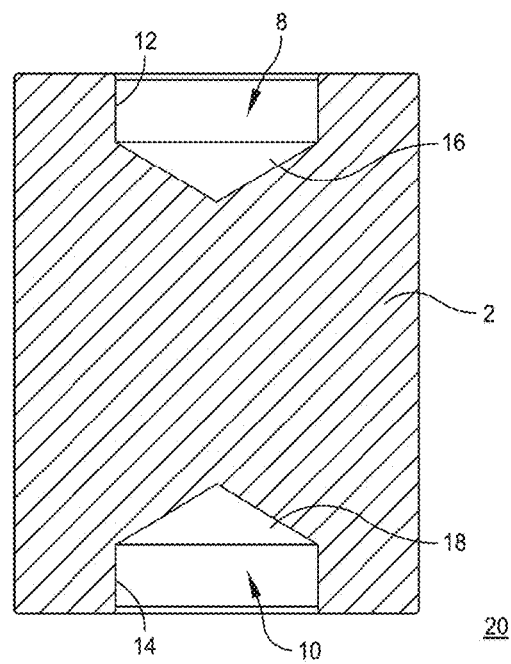
FIG. 3A is a schematic of a cut-out side view, as defined in FIG. 2A, of a solid-core ring-magnet having a cylindrical shape.

A cross section of the magnet previously introduced in FIG. 2A is shown in FIG. 3A. Magnet 20 shown in this figure has top cavity 8 and bottom cavity 10. The portion of top cavity 8 that descends from top surface 4 toward the middle of the top cavity has a top ring shaped wall 12 and a top conical surface wall 16. The conical surface wall 16 is the portion of the cavity wall that has radii decreasing from that of the upper parts of the cavity wall to lower values until the cavity ends. Similarly shown are bottom cavity with bottom ring shaped wall 14 and bottom cavity conical surface 18. The shape of the cavity does not need to include a conical shape, and can be any shape ("V" shaped, "U" shaped or irregular shape) so long as it can receive the vessel, as described herein. The top and bottom cavities, or their portions such as the walls and surfaces, need not be the same as each other. However, having them the same makes it easier to assemble them on a guide plate as well as making substitution of a magnet with another one easy. For embodiments that have identically shaped top and bottom cavities, a decision during the assembly of the magnets on a guide plate as to whether they have the same or opposite polarity can be made by simply holding a random end of each of two magnets against each other. If they attract, they are oppositely polarized. If they repel, they share the same polarization.

Figure 3B:
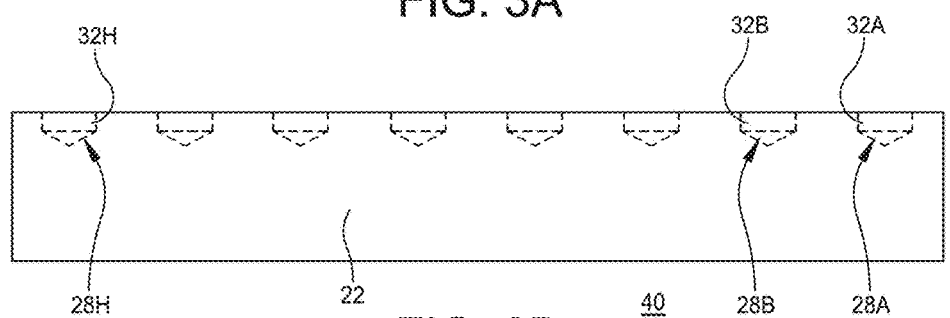
FIG. 3B is a schematic of a long-side view of a solid-core ring-magnet having multiple cylindrical/conical-shaped cavities and an overall rectangular-prism shape.
Figure 3C:
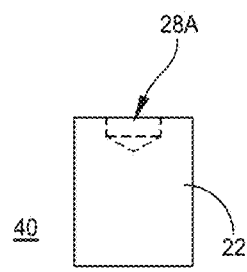
FIG. 3C is a schematic of a short-side view of a solid-core ring-magnet having multiple cylindrical/conical-shaped cavities and an overall rectangular-prism shape.

A side view showing the long side of block magnet 40 is shown in FIG. 3B. This figure shows side wall 22, top cavities (28A, 28B . . . 28H), and top cavity walls (32A, 32B . . . 32H). FIG. 3C shows the same magnet, but from the viewpoint of the short side.

Figure 4A:
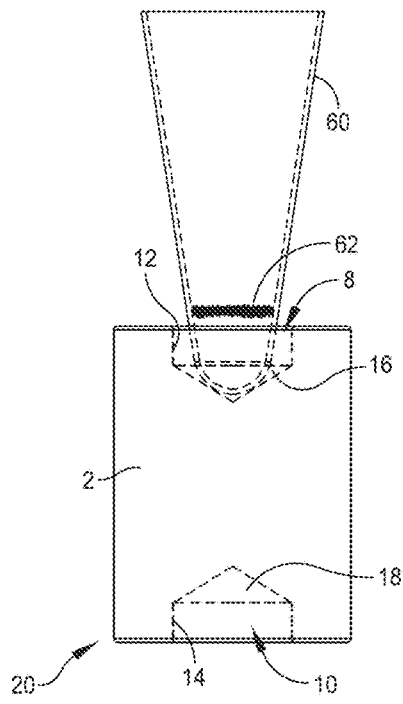
FIG. 4A is a schematic of a side view of a solid-core ring-magnet having a cylindrical shape, further showing two cavities and a V-shaped vessel for holding a reaction mixture of magnetic beads and macromolecules. The ring of complex between the magnetic beads and macromolecules just above the top of the magnet is shown.
Figure 4B:
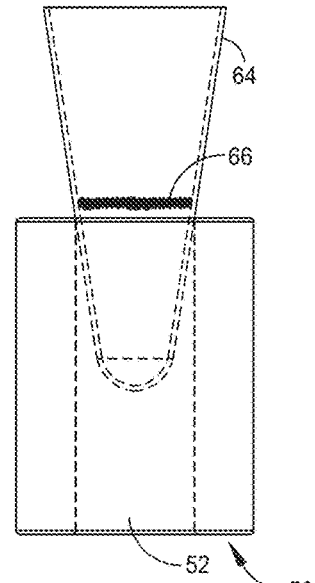
FIG. 4B is a schematic of a side view of a standard ring magnet having one full-length channel, and a V-shaped vessel for reaction mixture of magnetic beads and macromolecules. The ring of complex between the magnetic beads and macromolecules just above the top of the magnet is shown.
Figure 4C:
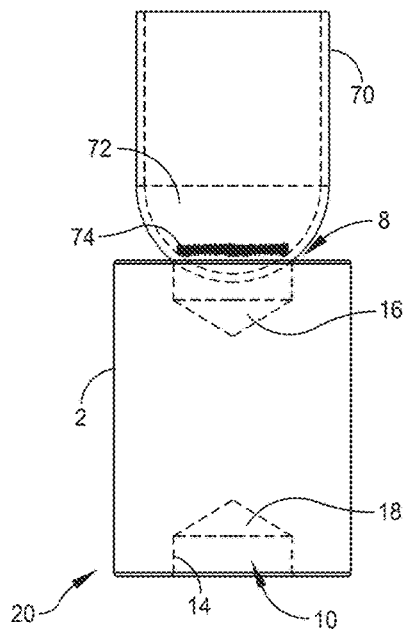
FIG. 4C is a schematic of a side view of a solid-core ring-magnet having a cylindrical shape, further showing two cavities and a U-shaped vessel for reaction mixture of magnetic beads and macromolecules. The ring of complex between the magnetic beads and macromolecules just above the top of the magnet is shown.
Figure 4D:
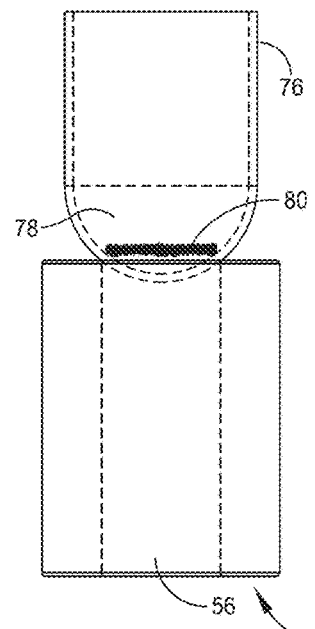
FIG. 4D is a schematic of a side view of a standard ring magnet having one full-length channel and a U-shaped vessel for reaction mixture of magnetic beads and macromolecules. The ring of complex between the magnetic beads and macromolecules just above the top of the magnet is shown.

A comparison between a previously available magnet (referred to as a "standard ring magnet") and the solid-core ring magnets of the present invention is shown in FIG. 4A through FIG. 4D. As should be immediately apparent, the standard ring magnet has a channel that runs through the entire thickness between the top and bottom ends of the magnet (FIG. 4B and FIG. 4D). In contrast, the solid-core ring magnet of the present invention, as the name implies, has a solid core and one or more cavities that do not create a channel/tunnel through the entire thickness of the magnet (FIG. 4A and FIG. 4C). Each of the cavities shown in FIG. 4A and FIG. 4C terminates with a conical surface. In this embodiment, a conical surface allows accommodation of a vessel that has a V-shaped bottom tip, whereas the diameter of the cavity above the conical surface allows accommodation of a vessel that has a U-shaped bottom tip. In striking contrast, while a standard magnet would lead to a high volume of sample being underneath the aligned level of the macromolecule, a solid-core ring magnet would allow a low volume of sample being underneath the aligned level of the macromolecule/bead complex. Nucleic acid/bead band 62 aggregates at a lower position in vessel 60 when using the solid core ring magnet of the present invention (See FIG. 4A), as compared to the position of the nucleic acid/bead band 66 in vessels 64 using the standard ring magnet (See FIG. 4B). A lower position in the well is desirable since less elution buffer is generally needed to elute the DNA, leading to a higher DNA concentration.

The terms U-shaped vessel, vessel with a U-shaped bottom tip, and round bottom shaped well are used interchangeable. The terms V-shaped vessel, vessel with a V-shaped bottom tip, and conical shaped well are also used interchangeably.

Overall, FIGS. 4A and 4C show conical shaped vessel 60 having a V-shaped bottom tip, nucleic acid/bead complex band 62, round shaped vessel 70, nucleic acid solution 72, and nucleic acid band 74. For comparison, FIGS. 4B and 4D show standard ring magnet 50 having standard channel/tunnel 52, which is used for V-shaped vessel 64 to isolate nucleic acid 66, and standard ring magnet 54 having standard channel 56, which is used for U-shaped vessel 76 to isolate nucleic acid 80 from solution 78. As can be seen in the figures, the standard ring magnet of FIG. 4B causes the nucleic acid/bead complex to sit higher in the vessel, as compared to the nucleic acid/bead complex shown in FIG. 4A. Accordingly, less elution buffer is needed when using the solid core ring magnet of the present invention.

Additionally, FIGS. 4A and 4C show that the solid core ring magnet of the present invention is universal with respect to the type of vessel being used. It can be used with a "V" shaped vessels such as a PCR plate or a "U" shaped vessel such as a deep-well plate. Since either vessel shape can be used, the solid core magnet plate can be used to perform several experiments or purification steps without having to switch to another magnet plate having a different size/shaped magnet.

Even though the macromolecule is specifically a nucleic acid (e.g., DNA, RNA, PNA) in these figures, also included in other embodiments are other macromolecules such as proteins (e.g., antibodies, peptides). Essentially, any macromolecule that can be made to adhere, reversibly or not, to magnetic beads can be subjected to the methods disclosed herein.

Figure 4E:
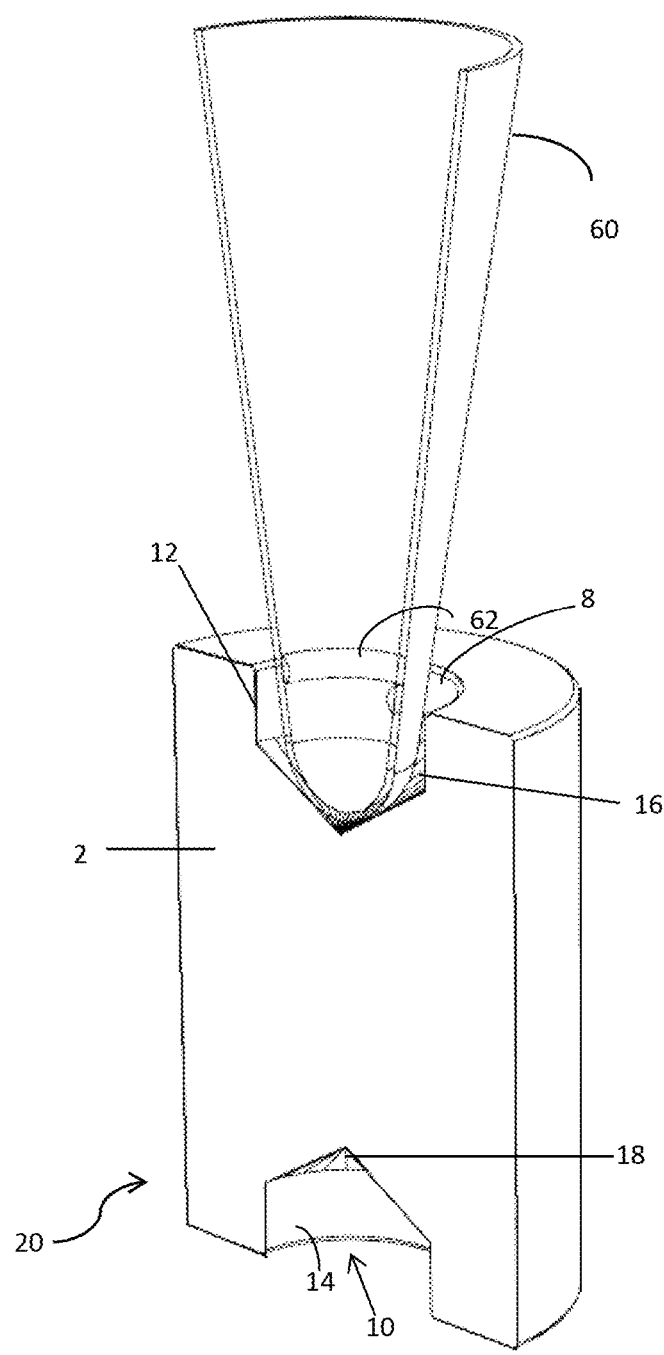
FIG. 4E is a schematic of a perspective view of a of a solid-core ring-magnet having a cylindrical shape, further showing two cavities and a V-shaped vessel for holding a reaction mixture of magnetic beads and macromolecules shown in FIG. 4A. The ring or band of macromolecule/bead complex just above the top of the magnet is shown.
Figure 4F:
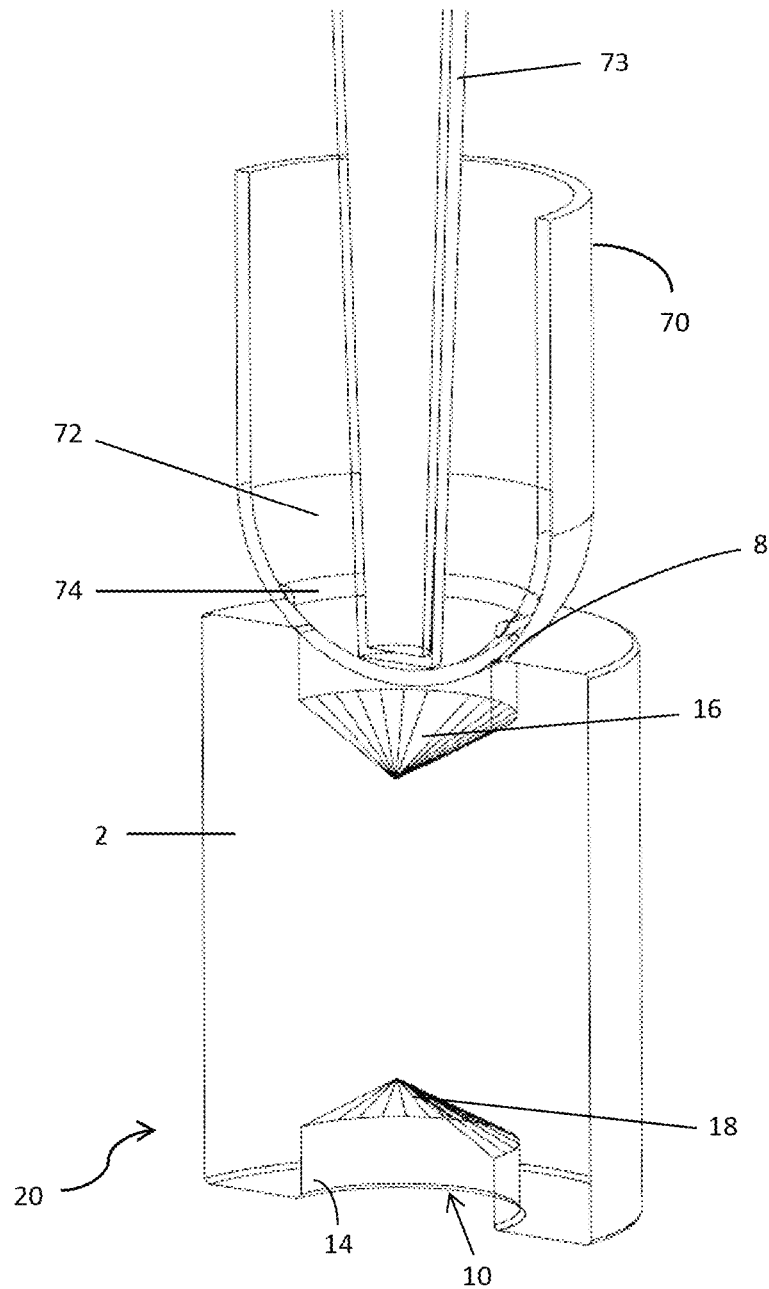
FIG. 4F is a schematic of a perspective view of a of a solid-core ring-magnet having a cylindrical shape, further showing two cavities and a U-shaped vessel for holding a reaction mixture of magnetic beads and macromolecules shown in FIG. 4B. The ring or band of macromolecule/bead complex just above the top of the magnet is shown and also a pipette is shown.

Now turning to FIGS. 4E and 4F, the formation of the nucleic acid/bead complex can be seen. FIG. 4E is a cross-sectional view of FIG. 4A and FIG. 4F is a cross-sectional view of FIG. 4C. FIG. 4E shows the aggregation of the nucleic acid/bead band 62 and FIG. 4F shows the aggregation of nucleic acid/bead band 74. As can be seen from this drawing, the band forms a ring along the inner wall of vessels 60 or 70. The formation of the nucleic acid/bead band in a ring shape is a function of the magnetic fields emitted by the solid core ring magnet, which are further described herein. Since a ring is formed along the inner vessel wall, pipetting the supernatant out (for example using pipette 73), whether in an automated fashion or manually, is easily performed and allows one to leave the bead band in the vessel.

The location of the macromolecule ring band impacts the steps of the methodology for separating the macromolecules from the mixture. When the vessel is placed on the magnet, the magnetic beads in the solution aggregate near the magnet at the place of the highest concentration of the magnetic field lines; this is where the magnetic field is generally the strongest. Since the upper portion of the cavity wall is in the shape of a ring the beads form a ring in the bottom of the vessel, near the top of the magnet. After discarding the supernatant and washing the immobilized beads with a wash solution, the next step is intended to recover the macromolecules from the beads. This is accomplished by exposing the beads to elution buffer, which will reverse the adherence between the macromolecules and the beads. The purified macromolecules are then present in the elution buffer, which can subsequently be removed from the vessel by aspiration. To effectively elute the macromolecules from the beads, one has to add enough elution buffer to completely cover the beads with buffer, so that effective elution can take place. At the same time, one wants to keep the volume of elution buffer as small as possible so as not to dilute the macromolecules unnecessarily. The volume needed is kept low because the magnet of the present invention is designed in such a way that the ring of beads will form as low as possible inside the vessel, regardless of the shape of the vessel.

Figure 5A:
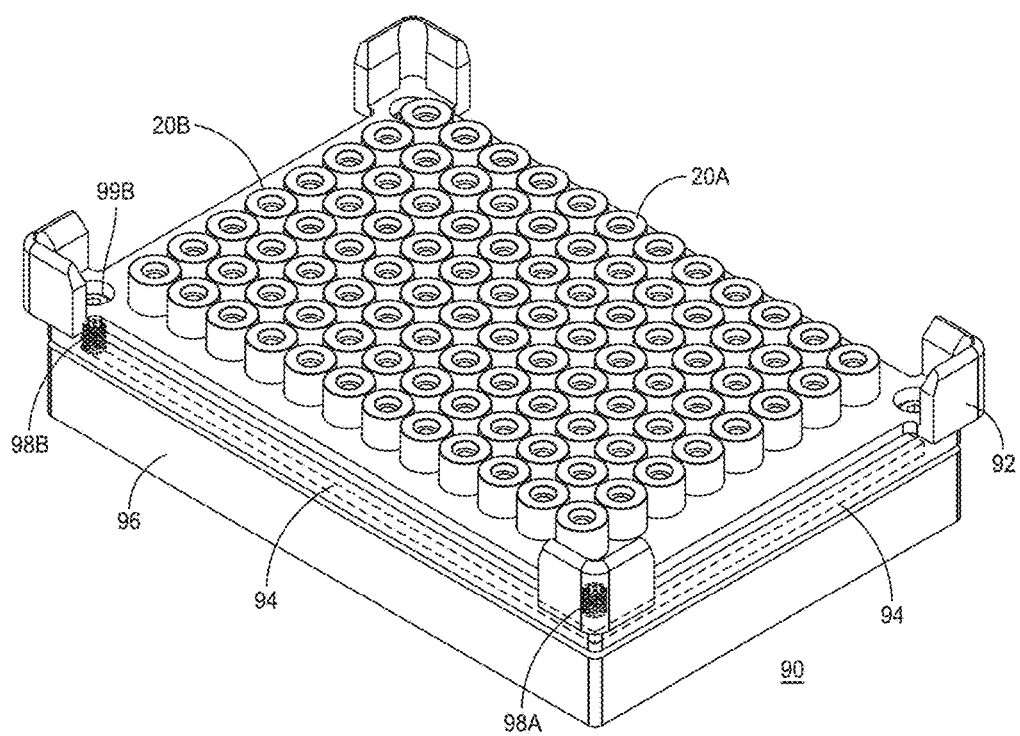
FIG. 5A is a schematic of a perspective view of a magnet plate having multiple solid-core ring-magnets that each has a cylindrical shape.

Magnetic field lines are created by the magnets. The lines emanate from one side of the magnet and terminate on the other. The direction of the magnetization is generally perpendicular to the surface(s) with the cavities, in other words, along the axis of the cavities. In particular, the magnets disclosed herein are magnetized through the thickness (i.e., along the center axis running between the top surface plane and the bottom surface plane). Each cavity is surrounded by a top surface and a bottom surface, and each such side (top surface and bottom surface) has a certain polarity, which can be designated as north (N) or south (S). When the magnets having an overall cylindrical shape are assembled on a guide plate (an example of which is shown in FIG. 5A), they can be arranged in any number of arrangements including alternating rows, alternating columns, checkerboard arrangement or other pattern. Arrangements of polarities are embodied for any top plates that might have a different number of magnet receivers to accommodate various size plates (e.g., 6, 24, 96, 384 or even 1536 sample wells arranged in a 2:3 ratio rectangular matrix).

Because the shape of the solid-core ring-magnet is different than that of a standard ring-magnet with a channel/tunnel running through the entire thickness of the magnet, the magnetic field lines created are different. In the solid-core ring magnet, the lines pass closer to the body of the magnet and result in stronger pull forces because of the increased amount of magnetic material. Experimental support for this is provided in the exemplification section, Experiment 1 and in FIG. 6. Stronger pull forces facilitate quicker recovery of material, and also facilitate recovery of higher yields of material. See Experiment 2, FIG. 7.

FIG. 5A shows magnet plate 90, within which there is top plate 82 (also referred to as guide plate) that has 96 magnet receivers (i.e., the holes not shown in the figure, which receive the magnets). The magnet receivers are arranged along 8 rows and 12 columns. Each magnet receiver receives a magnet (e.g., 20A, 20B). Springs (98A, 98B, etc.) are placed around shoulder posts (99B, etc.) at the corners of the top plate. The shoulder posts, and the springs, pass through top plate 92 and base plate 96. The springs allow flexibility in the leveling of the magnets, and thus any vessels placed in their cavities. With the springs, pipetting from the vessels can be accomplished more efficiently. In an embodiment, support plate 94 is a metal, and an affinity exists between the support plate and the magnets. Further underneath, below both the top plate and the support plate, is base plate 96. The top plate can be fastened to the base plate by inserting shoulder posts (e.g., bolts) through the shoulder bolt receivers found at the corners of the two plates. In some embodiments, the shoulder bolts and the springs can be on each of the four corners of the plates, whereas in other embodiments they can be in alternative locations (e.g., along portions of the edges or on some of the corners only). The support plate is made from a material that has affinity to magnets. It can be from a metal such as iron, nickel, cobalt, or an alloy of different materials.

Figure 5B:
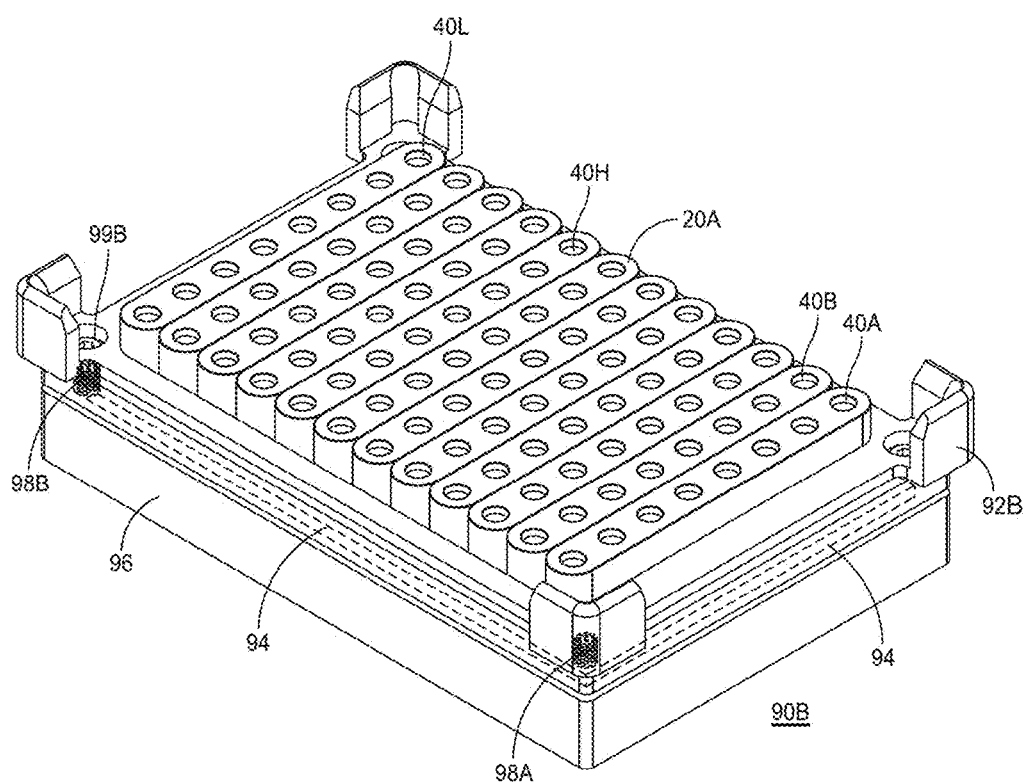
FIG. 5B is a schematic of a perspective view of a magnet plate having multiple solid-core ring-magnets that each has multiple cylindrical/conical-shaped cavities and an overall rectangular-prism shape.

In a similar fashion to FIG. 5A, FIG. 5B shows a magnet plate. In this embodiment, the magnets are block shaped. Similar elements, such as the three plates (top, support, base), springs, and shoulder posts are usable with this embodiment. While not necessary, in the embodiment shown, all components except the magnets and the top plate are the same as in FIG. 5A.

The integrated spring components enable complete liquid removal without tip occlusion. The springs effectively cushion the wells, and allow the plates (e.g., top plate, support plate) to give way when tips (e.g., pipette tips) come in contact with a well bottom. This compensates for physical tolerances between labware and pipettors, each of which can otherwise compromise the precision of supernatant removal (e.g., aspiration). In addition, in some embodiments the magnet plates are designed for automation; they have a standardized footprint to fit into standard liquid handler plate nests, plate hotels, and stackers. Gripper grooves on the long sides provide space for robotic arms or grippers when moving microplates onto and off the magnet plates.

The solid-core ring-magnet, when used for isolating macromolecules, allows quicker recovery of the macromolecules, recovery of higher percentages, and recovery of the macromolecules in smaller elution volumes. The solid core ring magnet, as described in the example, provides for better separation of the beads from the mixture. This is accomplished because the solid core magnet provides additional force that is applied to the magnetic beads. In an embodiment, the solid core provides between about 1% and about 25% (e.g., about 20%, 15%, 10%, and 5%) additional magnetic force, as compared to the standard ring magnet. See FIG. 6. The additional force provides for better, more efficient separation. Accordingly, the magnet of the present invention has a recovery of the macromolecules between about 40% to about 99% (e.g., about 45%, 50%, 60%, 65%, 70%, 75%, 80%, 85%, 90%, and 95%) recovery. As compared to a non-solid core magnet (e.g., a standard ring magnet), the magnet of the present invention improves recovery by about 1% to about 60% (e.g., about 5%, 10%, 15%, 20%, 25%, 30%, 35%, 40%, 45%, 50%, and 55%).

Specifically, the magnet of the present invention is able to separate more nucleic acid material and is able to do so faster and in fewer cycles, as compared to the standard ring magnet. In an embodiment, the magnet of present invention is able to separate macromolecules that can adhere to magnetic beads in an amount that is 1× faster and up to 4.5 times faster, as compared to a non-solid core magnet (e.g., a standard ring magnet as shown in FIGS. 4B and 4D). Experimental support for these improved properties is provided in the exemplification section and in FIGS. 7A through 7J.

Standard conditions for forming the macromolecule-bead complex are known in the art and can be found, for example, in Rohland, et al., Cost-Effective High-Throughput DNA Sequencing Libraries For Multiplexed Target Capture, *Genome Research* 22:939-946 and Supplemental Notes (the entire teachings of which are incorporated herein by reference). For example, reagent kits that can be used to form the macromolecule-bead complex are commercially available, such as the AMPURE composition from Beckman Coulter, or such reagents can be made. One example of a solid phase reversible immobilization reagent that can be made and used with the present invention is a MagNA composition, which is made from:
- 0.1% carboxyl-modified Sera-Mag Magnetic Speed-beads (FisherSci, cat.#: 09-981-123)
- 18% PEG-8000 (w/v) (e.g. Sigma Aldrich, cat.#: 89510)
- 1M NaCl
- 10 mM Tris-HCl, ph 8.0
- 1 mM EDTA, pH 8.0
- Optional: 0.05% Tween 20

To form the macromolecule-bead complex, in one embodiment, 0.5×-3× MagNA in an amount ranging from 10 microliters to 400 microliters can be added to the mixture.

EXEMPLIFICATION

Introduction:

Magnetic-bead-based nucleic acid purification is a standard technique in high-throughput sequencing. Purification steps occur at various points in the sample preparation workflow, from the original extraction of DNA out of a biological sample, to enzymatic conditioning steps, PCR cleanup, and size selection. To enable automated processing, the samples are usually transferred from a primary container, like a collection tube, Eppendorf vial or the like, to a microplate. Microplates exist in many different specialized formats from 6 wells (2×3) to several thousand wells. The most common format is the 96-well plate, wherein the wells, i.e. the individual cavities holding the samples, are arranged in an 8×12 array. Aside from the number of wells, microplates can vary greatly with regard to the volume per well, the shape of the wells, the materials used, and other parameters depending on the intended application. Despite all their differences, industry groups have agreed to a set of parameters defining certain dimensions of microplates with the goal of maintaining their suitability for automated processing in standard robotic lab instruments. These standards are maintained by the Society for Lab Automation and Screening (SLAS) and can be downloaded from their website at www.slas.org/resources/information/industry-standards. The basic principle of magnetic bead separations includes the sequestration of magnetic beads from the reaction matrix by exposing them to a magnetic field. The magnetic force then immobilizes the beads, allowing supernatant to be removed while the beads, with their attached payload, are retained.

The most common way of applying a magnetic field is achieved by placing the microplate on top of a magnet plate that complements the microplate. Magnet plates are arrangements of permanent magnets in an array similar to the array of wells of the microplate types for which they are made. Just like there are various microplate types—with 24 wells, 96, 384 and so on, there are different magnet plates as well. Some magnet plates use post magnets, where one post magnet is located in the center of 4 wells; also available are plates with bar magnets, where each bar magnet serves an entire row or column of wells of a microplate. A type of magnet plate is a ring magnet plate with 96 ring-shaped permanent magnets. The ring shape cavity is particularly useful because it produces a ring-shaped magnetic field, causing the magnetic beads to aggregate in the same ring shape in the bottom of the microplate well. In this process, an area in the center of the ring remains bead-free, allowing a pipet tip to reach the well bottom and aspirate all liquid without disturbing the magnetic beads.

With the microplate still on the magnet, the beads are allowed to dry before elution buffer is added to release the DNA from the beads. It is important to note that the volume of elution buffer necessary to achieve complete elution must be sufficient to cover the beads entirely; if a bead does not come into contact with elution buffer, the DNA will stay on the bead. At the same time, it is desirable to keep the elution volume as low as possible so as not to unnecessarily dilute the product (e.g. the purified, eluted DNA).

The minimum elution volume is a function of the location of the bead ring inside the well. Lower bead rings allow for smaller elution volumes. FIGS. 4A and 4B show how the position of the bead ring depends on the geometry of the well and the magnet. The PCR well in FIG. 4B enters the ring magnet significantly lower than the PCR well in FIG. 4A. In an embodiment as shown in FIG. 4B, the elution volume to cover the beads is about 35 µl. This is especially problematic because PCR plates, which have a well volume of only about 150-200 µl, are sometimes used for low volume reactions with low amounts of DNA. Eluting small amounts of DNA in larger volumes of elution buffer may lead to unacceptably low DNA concentrations.

Other possible approaches use adapters between the magnet plate (with ring magnets sized for round bottom wells as in 4D) to support a PCR plate. While viable in individual cases; the significant disadvantage is that the adapter relies on specific PCR plate geometries; in other words, it is not a universal solution but only works with certain PCR plate types.

On the contrary, the solid core ring magnet is universal and achieves low elution volumes. The solid core ring magnet of the present invention also separates the macromolecule/magnet beads faster and with more recovery, as compared to standard ring magnets. The following experiments were designed to demonstrate the application of the solid core ring magnet.

To verify the expected gain in performance, two experiments were conducted.

Experiment 1: Comparison of the Pull Force Between a Solid Core Ring Magnet and a Standard Ring Magnet A solid-core ring magnet and a standard ring-magnet were manufactured with the properties shown in Table 1.

TABLE 1

| Magnet Properties | | |
|---|---|---|
| | Solid Core Ring Magnet | Standard Ring Magnet |
| Outer Diameter | 8.6 mm | 8.6 mm |
| Inner Diameter | 4.3 mm to a depth of 2.5 mm, on both sides | 4.3 mm through |
| Thickness (Height) | 11.5 mm | 11.5 mm |
| Magnetic Grade | N50, NdFeB | N50, NdFeB |
| Magnetization | Through the Thickness | Through the Thickness |
| Volume of Magnetic Material | 613.2855 mm$^3$ | 500.8373 mm$^3$ |

The Solid Core Ring Magnet contains about 22.45% more magnetic material than the regular ring magnet with the same outer dimensions. In an embodiment, the solid core ring magnet of the present invention has between about 10% to about 30% more magnetic material, as compared to a standard ring magnet.

After this, an experiment was performed to determine the differences in pull forces between the two magnets across different distances. The data was generated using a model ES30 test stand equipped with a force gauge Model M5-20 and a Mitutoyo travel gauge, model ESM001 (all Mark-10 Corporation, 11 Dixon Avenue, Copiague, N.Y. 11726, US).

Figure 6:
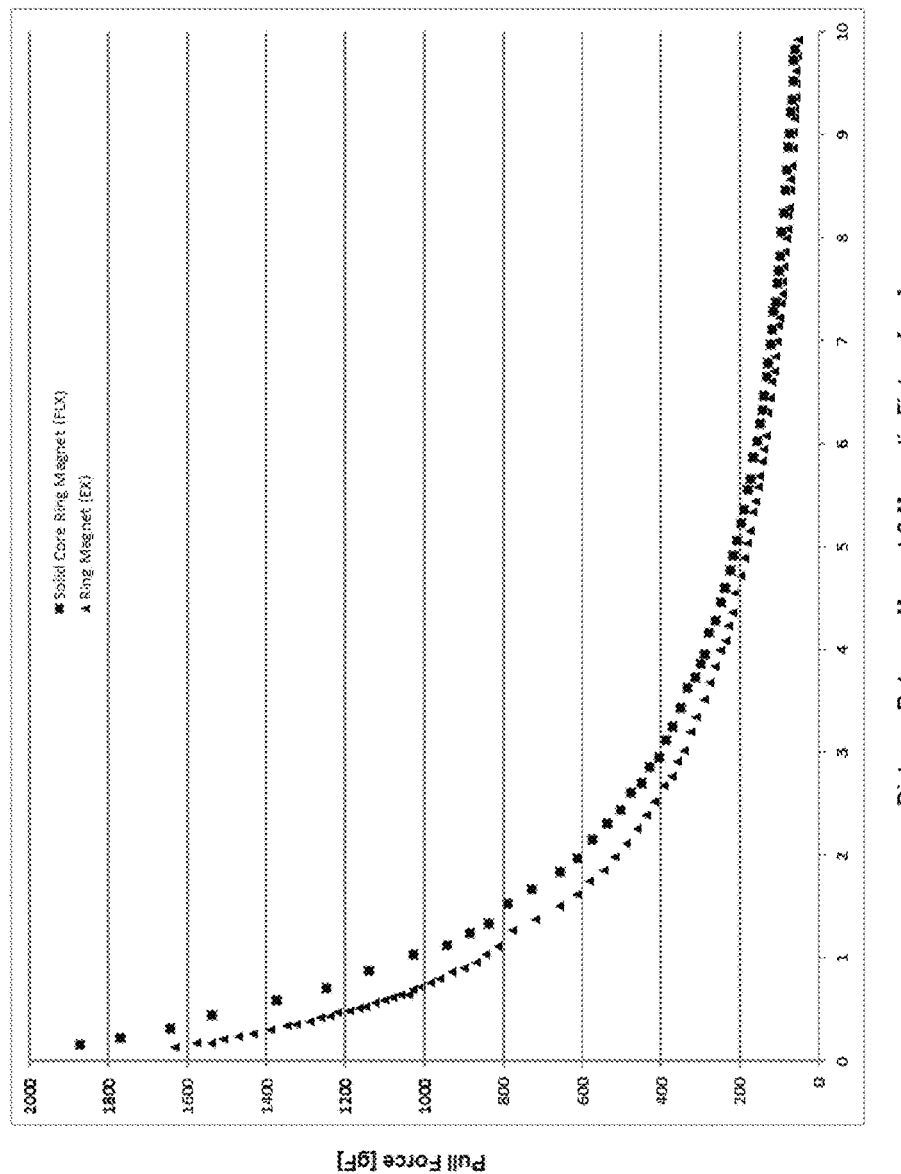
FIG. 6 is a line plot chart of differences in pull forces measured between a magnetic fixture and the solid core ring magnet (squares) or ring magnet (triangles). The measurement was done using a digital force gauge.

FIG. 6 shows the results for comparing pull forces between a magnetic fixture on one side and a solid core ring magnet or a standard ring magnet on the other side. Both of the magnets used were grade N50, NdFeB, 8.6 mm diameter, and 11.5 mm thick. The ring magnet had an inner diameter of 4.3 mm. The solid core ring magnet had two cavities, one on each side, with a diameter of 4.3 mm and a depth of 2.5 mm. Both magnets were magnetized through the thickness (i.e., along the center axis). As seen, for a certain distance value, especially for lower values of distances, the solid core ring magnet has a stronger pull force. Because both magnets are equivalent (same outer dimensions and magnetic grade) except that the standard magnet is drilled through all the way, the stronger pull forces in the solid core magnet result from the shape of the magnet, specifically the additional magnetic material present in the core of the solid core ring magnet.

FIG. 6 shows the pull force between the test magnet and the magnetic fixture. The magnetic fixture was the same in both tests.

Results:

Table 2 shows selected data points with the difference in pull force as % change.

| Standard Ring Magnet | | Solid Core Ring Magnet | | |
|---|---|---|---|---|
| Travel [mm] | Load [gF] | Travel [mm] | Load [gF] | % Difference |
| 35 | 2 | 35.05 | 2 | 0.0% |
| 33.5 | 2 | 33.5 | 2 | 0.0% |
| 32.08 | 2 | 32.08 | 2 | 0.0% |

-continued

| Standard Ring Magnet | | Solid Core Ring Magnet | | |
| --- | --- | --- | --- | --- |
| Travel [mm] | Load [gF] | Travel [mm] | Load [gF] | % Difference |
| 28.46 | 2 | 28.44 | 2 | 0.0% |
| 22.18 | 6 | 22.19 | 6 | 0.0% |
| 22 | 6 | 21.97 | 6 | 0.0% |
| 21.52 | 6 | 21.56 | 8 | 33.3% |
| 21.34 | 8 | 21.38 | 8 | 0.0% |
| 15.04 | 20 | 15.06 | 22 | 10.0% |
| 13.52 | 26 | 13.52 | 30 | 15.4% |
| 12.71 | 30 | 12.71 | 34 | 13.3% |
| 11.5 | 38 | 11.53 | 42 | 10.5% |
| 10.57 | 46 | 10.54 | 52 | 13.0% |
| 9.49 | 60 | 9.52 | 66 | 10.0% |
| 8.08 | 80 | 8.05 | 94 | 17.5% |
| 6.99 | 108 | 6.96 | 124 | 14.8% |
| 5.58 | 154 | 5.55 | 180 | 16.9% |
| 5.33 | 168 | 5.36 | 190 | 13.1% |
| 5.03 | 182 | 5.06 | 206 | 13.2% |
| 3.84 | 264 | 3.86 | 300 | 13.6% |
| 3.2 | 326 | 3.24 | 370 | 13.5% |
| 1.99 | 520 | 1.97 | 614 | 18.1% |
| 1.85 | 548 | 1.84 | 656 | 19.7% |
| 1.51 | 660 | 1.52 | 788 | 19.4% |
| 1.11 | 814 | 1.12 | 944 | 16.0% |
| 1.03 | 846 | 1.03 | 1028 | 21.5% |
| 0.86 | 930 | 0.87 | 1138 | 22.4% |
| 0.59 | 1102 | 0.58 | 1376 | 24.9% |
| 0.43 | 1240 | 0.44 | 1536 | 23.9% |
| 0.3 | 1390 | 0.31 | 1642 | 18.1% |
| 0.21 | 1510 | 0.22 | 1768 | 17.1% |
| 0.14 | 1634 | 0.15 | 1870 | 14.4% |

Table 2: Pull Force Comparison; Selected Data Points

Result:

A comparison of the pull force generated between a regular ring magnet D=8.6 mm, d=4.3 mm, and H=11.5 mm, and a solid core ring magnet of equivalent dimensions and grade shows significant differences in the range from 0 to about 15 mm of distance. The greatest difference was measured at 0.58 mm distance with 24.9%. (A difference reading of 33% shown near the top of the table, at about 21.5 mm of distance, is considered noise. The signal, i.e. the pull force measured, is low at this point, and the reading is surrounded on both sides by values of 0%.)

Experiment 2: Bead Separation Time Comparison

Additional experiments were performed to investigate the bead separation times for the different magnets.

As described herein, the detection method by which the present invention was compared to current plate based magnetic separation devices by spectrophotometry. In standard high-throughput NGS DNA sequencing workflows, each enzymatic process step is followed by a cleanup step where the DNA is selectively bound to iron cored beads through the addition of 0.1% carboxyl-modified Sera-Mag Speed-beads, 20% polyethylene glycol (PEG), and 2.5 M NaCl buffer in a mix ratio of 1.8× beads and buffer to 1× sample. The mixture is placed in a magnetic field, which pulls the beads and bound DNA to the sides of the well so that the reagents, washes and/or unwanted fragments can be removed as a supernatant. The percent of bound material captured and the time it takes for this capture to occur is of paramount importance for maintaining quality and throughput levels. Here we attempt to quantify this recovery metric without the need to test the efficiency of the capture chemistry. This was accomplished by simulating a given reaction volume at a set end point, by replacing enzymatic components with water while keeping the total reaction volume at 1.8× bead/PEG/NaCl mix: 1× sample. We do not expect that beads bound with DNA will move significantly different through the PEG/NaCl matrix than those unbound to DNA. A detailed procedure for bead detection:

A large quantity of 1.8×0.1% carboxyl-modified Sera-Mag Speed-beads (Thermo-Fisher Scientific, Pittsburgh Pa., USA, Cat number 09-981-123), 20% polyethylene glycol (PEG) (Sigma-Aldrich, St. Louis Mo., USA, Cat number 89510-250G-F), 2.5 M NaCl (Sigma-Aldrich, St. Louis Mo., USA, Cat number S6546-1L), 0.05% Tween-20 (Sigma-Aldrich, St. Louis Mo., USA, Cat number P9416-50 ML) and 1× water were premixed and set aside. A predetermined amount of bead/water mix was arrayed in groups of three per time point to either an Eppendorf twin.tec semi-skirted PCR plate (Eppendorf AG, Hamburg, Germany, Cat number 951020362) or a RK Riplate deep-well plate (BioExpress, Kaysville Utah, USA, Cat number 850356). Reaction volumes between 50-300 ul utilized the Eppendorf twin.tec plate and 500-2000 ul utilized the RK Riplate. Samples were arrayed in columns so that three samples were used for every end-point and all samples had a zero time point used as a control. End-points for 50-100 ul trials were 30 seconds-3 mins sampled in 30 second intervals, for 150-200 ul trials 30 seconds-5 min in 30 second intervals, for 200-750 ul trials 1 min-5 min in 30 second intervals, and for 1000-2000 ul trials 2.5-25 mins in 2.5 min intervals. Samples were arrayed using a 20-200 ul LTS multichannel pipette (Rainin Instruments LLC, Oakland Calif., USA, cat number L12-20XLS) or a 1000 ul single channel pipette (Gilson Inc., Middleton Wis., USA, cat number P1000). After arraying, the samples were left on the bench for exactly 5 minutes to simulate DNA binding time. The 96-well plate was then placed on the magnetic separator plate and a timer was started. At the set end-point all liquid was removed from the end point wells using a multichannel pipette with a smooth constant pipetting motion so as to cause as little disturbance to the formed bead ring as possible. Liquid was completely transferred to the corresponding wells of a second 96 well plate. All remaining time points of the same volume were processed in a similar manner. Transferred samples were then mixed 10× with a multichannel pipette to make sure any beads that may have settled had been completely resuspended. 50 ul, taken from the middle of transferred sample, was then aliquoted to the corresponding well of a 96 well flat bottomed plate (Thermo-Fisher Scientific, Pittsburgh Pa., USA, Cat number 12-565-501) for analysis.

Detection and Analysis Methods:

Samples and blanks were analyzed for absorbance based on published specifications using a Tecan Infinite 200 Pro Multiplate reader with i-control microplate reader analysis software (Tecan Group, Ltd, Männedorf, Switzerland) measuring absorbance at 560 nm. Samples were shaken in orbital mode at 3.5 amplitude for 3 seconds and then read at 25 flashes per well. All plates were read in duplicate and the resulting absorbance was averaged. Absorbance data was further analyzed using IMP 11.2 software (SAS, Cary N.C., USA) for consistency between data points. Absorbance readings obtained for the blank wells were averaged together and used as a normalization control for all wells containing sample. Total percent of beads captured was calculated as a reverse function of the normalized absorbance of beads remaining in solution divided by the total absorbance of beads present in the control, or zero, time point. Results were then plotted in Excel (Microsoft Corp, Redmond Wash., USA) against the results of similar volume points obtained using other magnetic separation devices.

TABLE 3

| | Time | Std. Ring Mag. | Solid Core Ring Mag. | % diff | | Time | Std. Ring Mag. | Solid Core Ring Mag. | % diff |
|---|---|---|---|---|---|---|---|---|---|
| 50 ul | 30 | 80.07667297 | 94.69176 | 15.43% | 100 | 30 | 37.23995636 | 70.81196 | 47.41% |
| | 1 | 95.43984145 | 98.15866 | 2.77% | | 1 | 74.19305795 | 94.99906 | 21.90% |
| | 1.5 | 95.93133422 | 98.35559 | 2.46% | | 1.5 | 92.06909531 | 98.67371 | 6.69% |
| | 2 | 98.13500867 | 98.81871 | 0.69% | | 2 | 96.47286979 | 99.03945 | 2.59% |
| | 2.5 | 98.34947811 | 99.6389 | 1.29% | | 2.5 | 97.81330423 | 98.88796 | 1.09% |
| | 3 | 98.28871191 | 99.40518 | 1.12% | | 3 | 98.69262933 | 99.60428 | 0.92% |
| 150 | 30 | 26.07026337 | 50.14476 | 48.01% | 200 | 30 | 19.39311039 | 40.41279 | 52.01% |
| | 1 | 58.09414013 | 87.10766 | 33.31% | | 1 | 40.63989389 | 79.76918 | 49.05% |
| | 1.5 | 74.4081237 | 96.27048 | 22.71% | | 1.5 | 51.16319869 | 93.50042 | 45.28% |
| | 2 | 91.05810939 | 98.5482 | 7.60% | | 2 | 71.00878141 | 96.39816 | 26.34% |
| | 2.5 | 94.28230152 | 99.46902 | 5.21% | | 2.5 | 82.93686286 | 97.83296 | 15.23% |
| | 3 | 94.93285923 | 99.67461 | 4.76% | | 3 | 89.07426608 | 98.66614 | 9.72% |
| | 3.5 | 97.76385719 | 99.67894 | 1.92% | | 3.5 | 92.52722613 | 98.97777 | 6.52% |
| | 4 | 96.78087165 | 99.58156 | 2.81% | | 4 | 94.01421458 | 99.10329 | 5.14% |
| | 5 | 98.59671404 | 99.77849 | 1.18% | | 5 | 92.9525902 | 99.53503 | 6.61% |
| 250 | 30 | 40.27648591 | 69.44254 | 42.00% | 300 | 30 | 31.69413085 | 65.15978 | 51.36% |
| | 1 | 59.90045115 | 89.61199 | 33.16% | | 1 | 48.70156597 | 84.5415 | 42.39% |
| | 1.5 | 68.49710442 | 95.17374 | 28.03% | | 1.5 | 57.02298399 | 93.05292 | 38.72% |
| | 2 | 80.3501216 | 96.40295 | 16.65% | | 2 | 66.49896343 | 95.38798 | 30.29% |
| | 2.5 | 87.17382752 | 98.30087 | 11.32% | | 2.5 | 76.29664731 | 97.13225 | 21.45% |
| | 3 | 90.64823436 | 98.90033 | 8.34% | | 3 | 82.53413641 | 97.63 | 15.46% |
| | 3.5 | 92.45692777 | 99.30069 | 6.89% | | 3.5 | 85.17211198 | 98.85488 | 13.84% |
| | 4 | 95.00196603 | 99.65343 | 4.67% | | 4 | 89.16481993 | 99.01394 | 9.95% |
| | 5 | 95.23430771 | 99.67508 | 4.46% | | 5 | 92.34254341 | 99.29203 | 7.00% |
| 500 | 30 | 34.52842754 | 78.66054 | 56.10% | 750 | 30 | 26.77121484 | 48.41286 | 44.70% |
| | 1 | 55.21212412 | 91.83777 | 39.88% | | 1 | 41.5258199 | 81.40246 | 48.99% |
| | 1.5 | 68.91535241 | 94.73334 | 27.25% | | 1.5 | 52.50342389 | 90.49603 | 41.98% |
| | 2 | 78.2893862 | 96.90827 | 19.21% | | 2 | 60.71564171 | 91.49368 | 33.64% |
| | 2.5 | 85.40605401 | 97.99248 | 12.84% | | 2.5 | 67.3773034 | 93.25959 | 27.75% |
| | 3 | 87.73410062 | 98.62873 | 11.05% | | 3 | 72.559085 | 95.53839 | 24.05% |
| | 3.5 | 90.52157227 | 98.6125 | 8.20% | | 3.5 | 77.22843141 | 97.18311 | 20.53% |
| | 4 | 92.32393149 | 98.51512 | 6.28% | | 4 | 84.04470492 | 94.31459 | 10.89% |
| | 5 | 93.04399126 | 99.04207 | 6.06% | | 5 | 85.71453813 | 97.83018 | 12.38% |
| 1000 | 2.5 | 47.65286868 | 86.54932 | 44.94% | 2000 | 2.5 | 34.71005201 | 63.42803 | 45.28% |
| | 5 | 83.80165204 | 97.45749 | 14.01% | | 5 | 59.59467814 | 86.48007 | 31.09% |
| | 7.5 | 91.55886375 | 98.35018 | 6.91% | | 7.5 | 77.52805007 | 93.11305 | 16.74% |
| | 10 | 92.38052749 | 98.53521 | 6.25% | | 10 | 79.11083052 | 94.19294 | 16.01% |
| | 12.5 | 95.53023817 | 98.59689 | 3.11% | | 12.5 | 83.89522614 | 95.7143 | 12.35% |
| | 15 | 96.76273362 | 98.42809 | 1.69% | | 15 | 87.78547741 | 94.21133 | 6.82% |
| | 17.5 | 97.02336867 | 98.00825 | 1.00% | | 17.5 | 89.66750789 | 96.04108 | 6.64% |
| | 20 | 97.28400404 | 99.08057 | 1.81% | | 20 | 87.96574837 | 97.4867 | 9.77% |
| | 22.5 | 96.58603189 | 99.85315 | 3.27% | | 22.5 | 90.59770681 | 96.22719 | 5.85% |
| | 25 | 97.83177987 | 99.65838 | 1.83% | | 25 | 91.97137297 | 98.01907 | 6.17% |

Figure 7A:
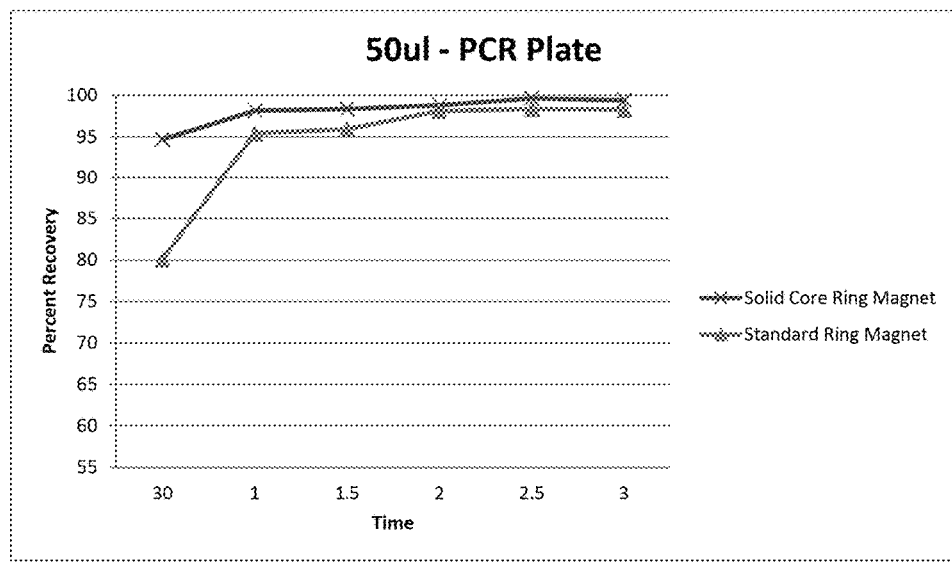
FIG. 7A is a line plot chart of the percent bead recovery over time from 50 microliters of solution in a PCR plate, showing the difference between a standard ring magnet (triangles) and a solid-core ring-magnet ("X") both having the same outer dimensions and magnetic grade.
Figure 7B:
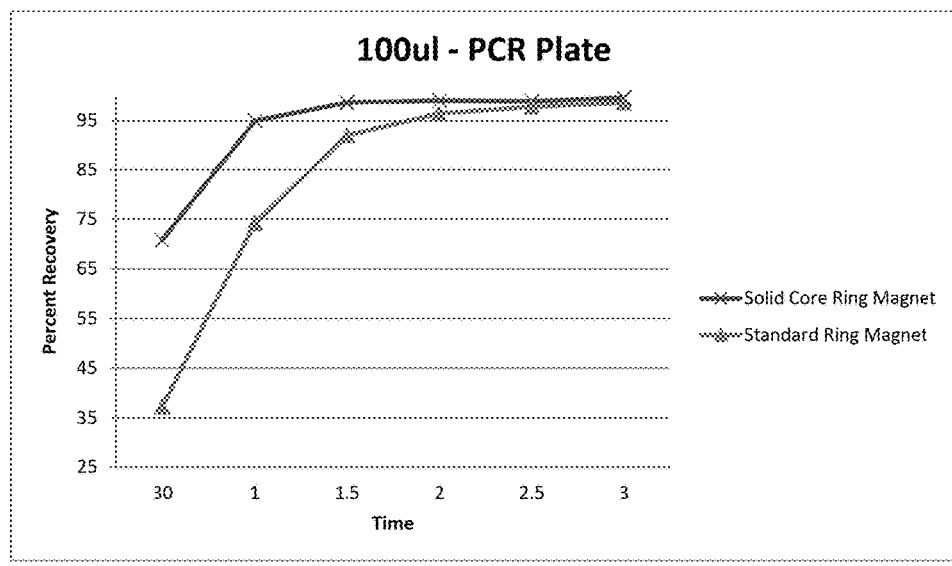
FIG. 7B is a line plot chart of the percent bead recovery over time from 100 microliters of solution in a PCR plate, showing the difference between a standard ring magnet (triangles) and a solid-core ring-magnet ("X") both having the same outer dimensions and magnetic grade.
Figure 7C:
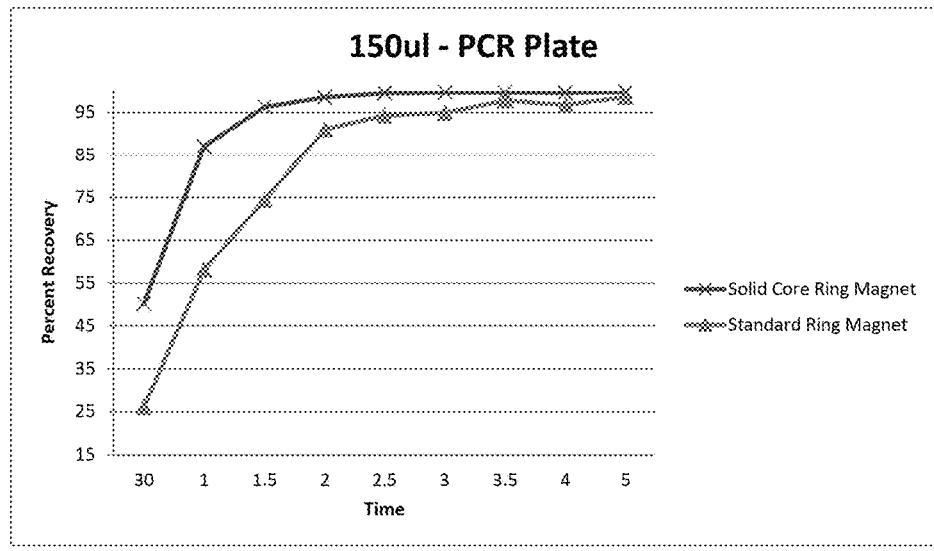
FIG. 7C is a line plot chart of the percent bead recovery over time from 150 microliters of solution in a PCR plate, showing the difference between a standard ring magnet (triangles) and a solid-core ring-magnet ("X") both having the same outer dimensions and magnetic grade.
Figure 7D:
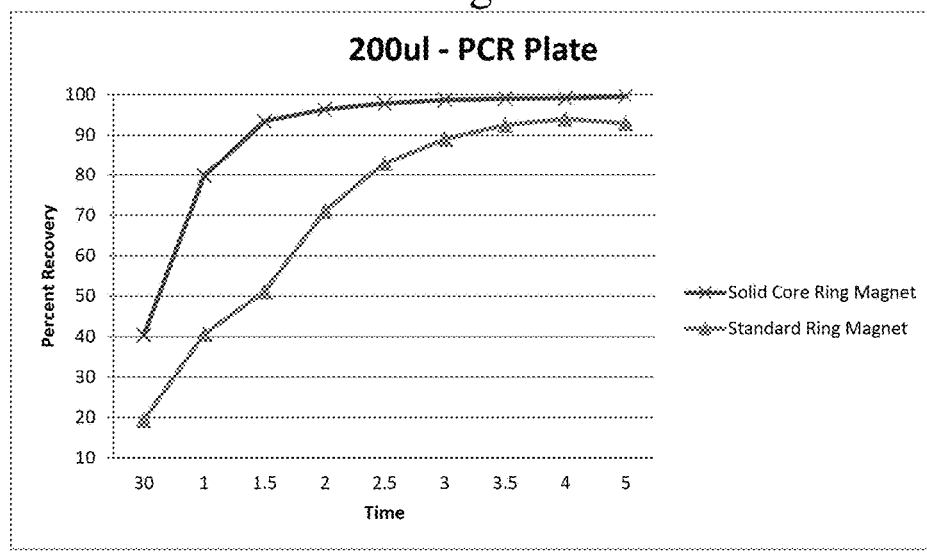
FIG. 7D is a line plot chart of the percent bead recovery over time from 200 microliters of solution in a PCR plate, showing the difference between a standard ring magnet (triangles) and a solid-core ring-magnet ("X") both having the same outer dimensions and magnetic grade.
Figure 7E:
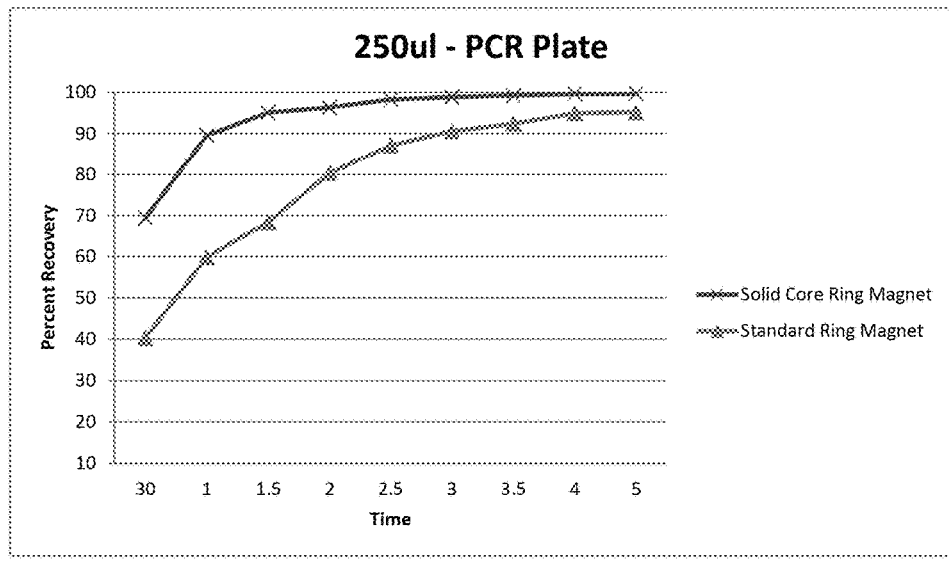
FIG. 7E is a line plot chart of the percent bead recovery over time from 250 microliters of solution in a PCR plate, showing the difference between a standard ring magnet (triangles) and a solid-core ring-magnet ("X") both having the same outer dimensions and magnetic grade.
Figure 7F:
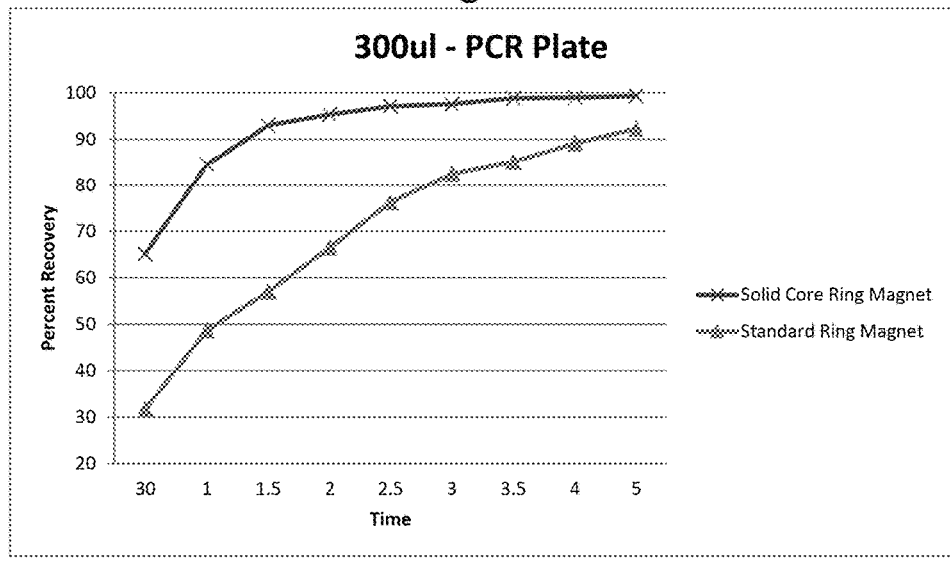
FIG. 7F is a line plot chart of the percent bead recovery over time from 300 microliters of solution in a PCR plate, showing the difference between a standard ring magnet (triangles) and a solid-core ring-magnet ("X") both having the same outer dimensions and magnetic grade.
Figure 7G:
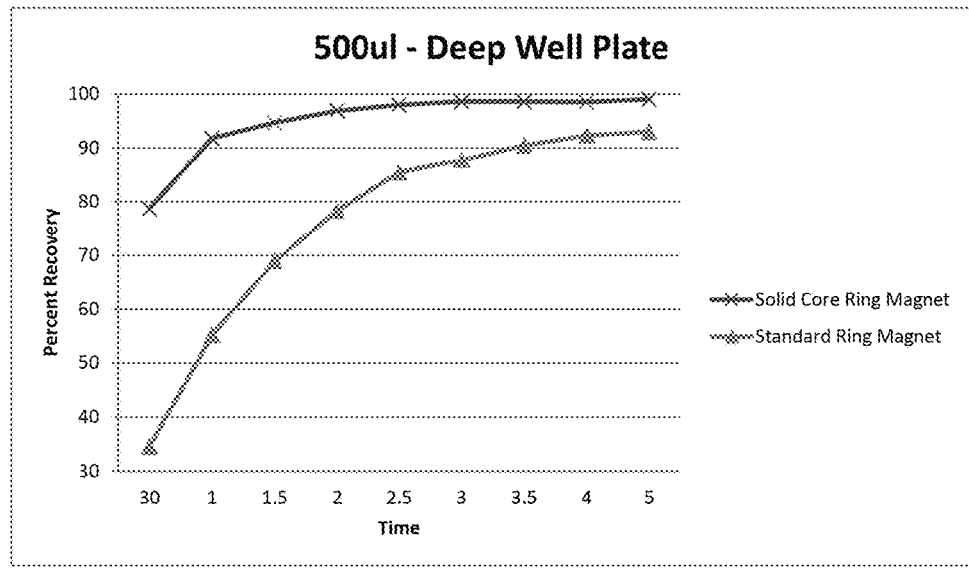
FIG. 7G is a line plot chart of the percent bead recovery over time from 500 microliters of solution in a deep well plate, showing the difference between a standard ring magnet (triangles) and a solid-core ring-magnet ("X") both having the same outer dimensions and magnetic grade.
Figure 7H:
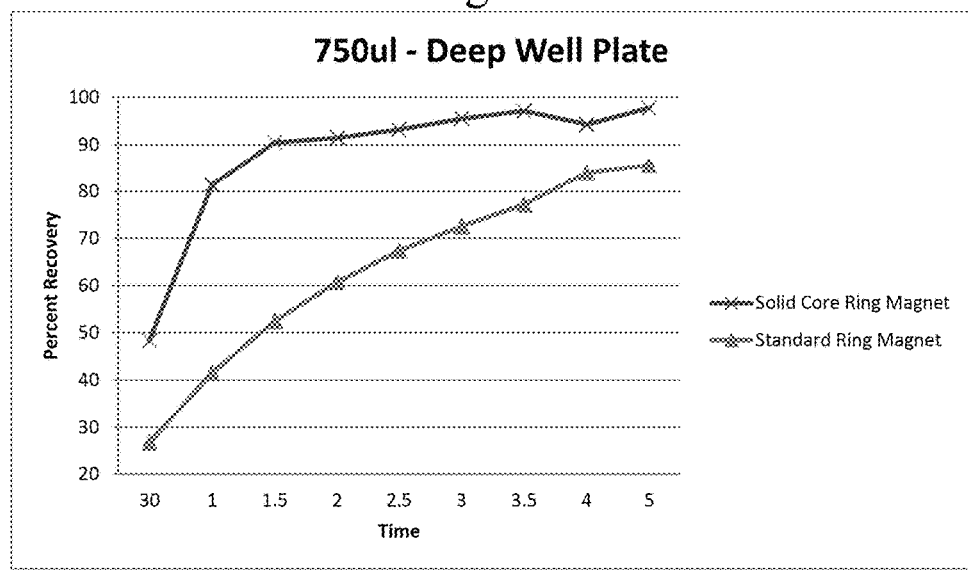
FIG. 7H is a line plot chart of the percent bead recovery over time from 750 microliters of solution in a deep well plate, showing the difference between a standard ring magnet (triangles) and a solid-core ring-magnet ("X") both having the same outer dimensions and magnetic grade.
Figure 7I:
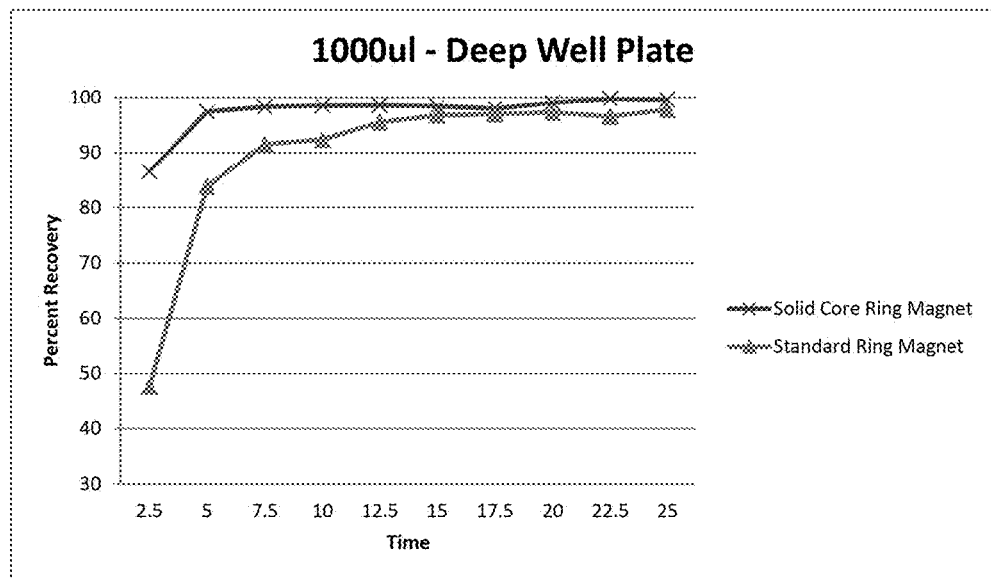
FIG. 7I is a line plot chart of the percent bead recovery over time from 1000 microliters of solution in a deep well plate, showing the difference between a standard ring magnet (triangles) and a solid-core ring-magnet ("X") both having the same outer dimensions and magnetic grade.
Figure 7J:
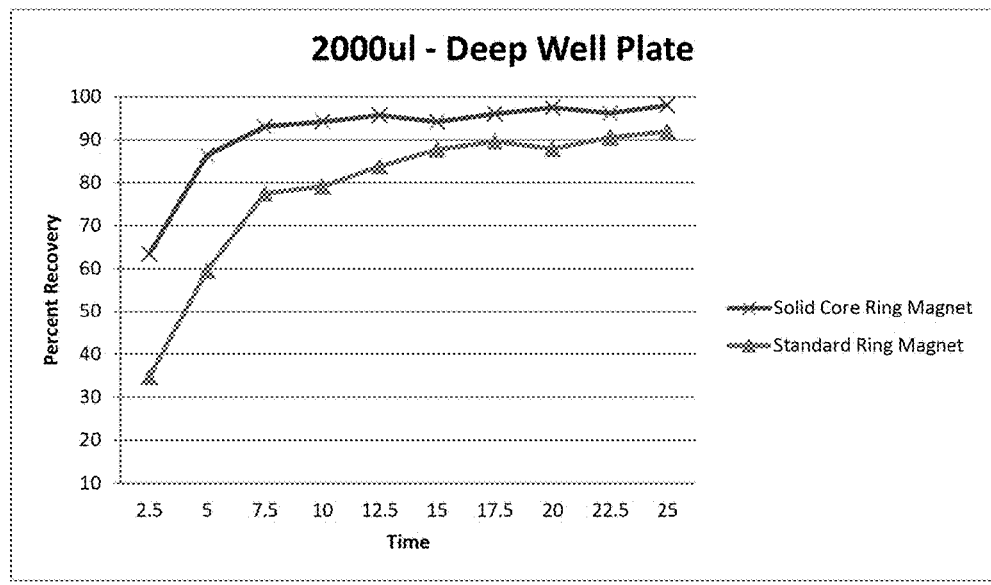
FIG. 7J is a line plot chart of the percent bead recovery over time from 2000 microliters of solution in a deep well plate, showing the difference between a standard ring magnet (triangles) and a solid-core ring-magnet ("X") both having the same outer dimensions and magnetic grade.

FIG. 7A shows the results for a 50 μL PCR plate, FIG. 7B for a 100 μL PCR plate, FIG. 7C for a 150 μL PCR plate, FIG. 7D for a 200 μL PCR plate, FIG. 7E for a 250 μL PCR plate, FIG. 7F for a 300 μL PCR plate, FIG. 7G for a 500 μL deep-well plate, FIG. 7H for a 750 μL deep-well plate, FIG. 7I for a 1000 μL deep-well plate, and FIG. 7J for a 2000 μL deep-well plate. In each of these results, especially for shorter attempted recovery times, it is clear that the percentage yield of the recovered beads is higher for a solid-core ring-magnet as compared to an equivalent ring-magnet. Similarly, when comparing similar amounts of recovery, it is clear that the solid-core ring-magnet allows recovery of a similar percentage within a shorter period of time.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for purifying macromolecules from a sample having a mixture in a vessel using a magnet wherein the macromolecules adhere to paramagnetic beads to form a complex under conditions to form a macromolecule-magnetic bead complex between the macromolecule and the magnetic beads; wherein the steps of the method comprise:
   a. separating the complex from the sample by placing the vessel at or near a cavity of the magnet; wherein the magnet comprises:
      i. a solid core having an inner mass of the magnet, a first end and a second end;
      ii. a first surface at or near the first end of the magnet;
      iii. a second surface at or near the second end of the magnet;
      iv. one or more cavities extending into the solid core at or near the first surface, the second surface, or both; wherein the one or more cavities each have a cavity wall and a portion of the cavity wall forms a ring shape;
      v. at least one side wall, wherein the side wall is in communication with the first surface and the second surface.

2. The method of claim 1, further comprising collecting the sample in a vessel.

3. The method of claim 1, further comprising adding magnetic beads to the sample.

4. The method of claim 1, wherein the step of separating the complex from the sample forms a supernatant; and the method further comprises the step of removing the supernatant.

5. The method of claim 1, further comprising the step of eluting the macromolecules from the magnetic beads.

6. The method of claim 1, wherein the sample comprises an extracellular matrix.

7. The method of claim 1, further comprising a step of lysing the sample before adding magnetic beads to the sample.

8. The method of claim 1, wherein a magnet volume enclosed between the first surface, the second surface, and the side wall forms a cylinder or a prism.

9. The method of claim 1, wherein the cavity wall surrounds the cavity between the first surface and at least a portion of the inner core, or between the second surface and at least a portion of the inner core.

10. The method of claim 1, wherein the cavity wall comprises a base surface, wherein the base surface covers portions of the cavity not covered by the portion of the wall having a ring-shape.

11. The method of claim 10, wherein the base surface forms a conical shape, a "U" shape, or an irregular shape.

12. A method for separating macromolecules from a sample having a mixture in a vessel using a magnet wherein the macromolecules adhere to paramagnetic beads to form a complex under conditions to form a macromolecule-magnetic bead complex between the macromolecule and the magnetic beads; wherein the steps of the method comprise:
   a. placing the vessel at or near a cavity of the magnet to thereby separate the complex from the sample; wherein the magnet comprises:
      i. a solid core having an inner mass of the magnet, a first end and a second end;
      ii. a first surface at or near the first end of the magnet;
      iii. a second surface at or near the second end of the magnet;
      iv. one or more cavities at or near the first surface, the second surface, or both; wherein the one or more cavities each have at least a portion of a cavity wall that has a shape configured to form a magnetic field within a vessel when the vessel in use and is placed at or near the cavity;
      v. at least one side wall, wherein the side wall is in communication with the first surface and the second surface.

13. The method of claim 12, further comprising collecting the sample in a vessel.

14. The method of claim 12, further comprising adding magnetic beads to the sample.

15. The method of claim 12, wherein the step of placing the vessel at or near a cavity of the magnet forms a supernatant; and the method further comprises the step of removing the supernatant.

16. The method of claim 12, further comprising the step of eluting the macromolecules from the magnetic beads.

17. The method of claim 12, wherein the sample comprises an extracellular matrix.

18. The method of claim 12, further comprising a step of lysing the sample before adding magnetic beads to the sample.

19. The method of claim 12, wherein a magnet volume enclosed between the first surface, the second surface, and the side wall forms a cylinder or a prism.

20. The method of claim 12, wherein the cavity wall surrounds the cavity between the first surface and at least a portion of the inner core, or between the second surface and at least a portion of the inner core.

21. The method of claim 12, wherein the cavity wall comprises a base surface.

22. The method of claim 21, wherein the base surface forms a conical shape, a "U" shape, or an irregular shape.

* * * * *